(12) United States Patent
Muthukumar et al.

(10) Patent No.: US 10,413,529 B2
(45) Date of Patent: *Sep. 17, 2019

(54) METHODS OF INHIBITING CATARACTS AND PRESBYOPIA

(71) Applicant: UNIVERSITY OF MASSACHUSETTS, Boston, MA (US)

(72) Inventors: Murugappan Muthukumar, Amherst, MA (US); Benjamin Mohr, Amherst, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/581,349

(22) Filed: Apr. 28, 2017

(65) Prior Publication Data

US 2017/0231905 A1 Aug. 17, 2017

Related U.S. Application Data

(63) Continuation of application No. 14/943,471, filed on Nov. 17, 2015, now Pat. No. 9,675,589, which is a continuation of application No. 14/772,254, filed as application No. PCT/US2014/027852 on Mar. 14, 2014, now Pat. No. 9,789,091.

(60) Provisional application No. 61/782,860, filed on Mar. 14, 2013.

(51) Int. Cl.
| | |
|---|---|
| *A61K 31/765* | (2006.01) |
| *A61P 27/10* | (2006.01) |
| *A61K 31/4188* | (2006.01) |
| *A61K 9/00* | (2006.01) |
| *A61K 9/06* | (2006.01) |
| *A61K 31/195* | (2006.01) |
| *A61K 31/20* | (2006.01) |
| *A61M 37/00* | (2006.01) |
| *A61N 1/32* | (2006.01) |
| *A61K 31/4015* | (2006.01) |

(52) U.S. Cl.
CPC ........ *A61K 31/4188* (2013.01); *A61K 9/0048* (2013.01); *A61K 9/06* (2013.01); *A61K 31/195* (2013.01); *A61K 31/20* (2013.01); *A61K 31/4015* (2013.01); *A61K 31/765* (2013.01); *A61M 37/0092* (2013.01); *A61N 1/325* (2013.01); *A61M 2037/0007* (2013.01); *A61P 27/10* (2018.01)

(58) Field of Classification Search
CPC .. A61K 9/0048; A61K 8/0072; A61K 31/765; A61K 9/0051; A61K 31/77; A61K 31/74; A61K 31/785
See application file for complete search history.

(56) References Cited

U.S. PATENT DOCUMENTS

| | | | |
|---|---|---|---|
| 4,351,826 A | 9/1982 | Clark et al. | |
| 4,526,789 A | 7/1985 | Clark et al. | |
| 4,620,979 A | 11/1986 | Schachar | |
| 4,665,089 A | 5/1987 | Siezen et al. | |
| 4,771,036 A | 9/1988 | Pigiet et al. | |
| 4,808,182 A | 2/1989 | Barrett | |
| 5,055,291 A | 10/1991 | Lam et al. | |
| 5,091,421 A | 2/1992 | Clark et al. | |
| 5,227,382 A | 7/1993 | Aziz et al. | |
| 5,338,545 A | 8/1994 | Clark et al. | |
| 5,375,611 A | 12/1994 | Lindqvist et al. | |
| 5,614,587 A * | 3/1997 | Rhee | A61K 47/61 525/54.1 |
| 5,658,592 A | 8/1997 | Tanihara et al. | |
| 5,672,662 A | 9/1997 | Harris et al. | |
| 5,756,672 A | 5/1998 | Builder et al. | |
| 5,807,944 A * | 9/1998 | Hirt | C08F 290/02 351/159.04 |
| 5,817,630 A | 10/1998 | Hofmann et al. | |
| 6,027,745 A | 2/2000 | Nakada et al. | |
| 6,103,756 A | 8/2000 | Gorsek | |
| 6,291,466 B1 | 9/2001 | Gwon et al. | |
| 6,294,518 B1 | 9/2001 | Potter et al. | |
| 6,835,394 B1 | 12/2004 | Discher et al. | |
| 6,945,971 B1 | 9/2005 | Gwon | |
| 6,958,224 B2 | 10/2005 | Kumar et al. | |
| 7,741,311 B2 | 6/2010 | Mousa et al. | |
| 7,767,429 B2 | 8/2010 | Bookbinder et al. | |
| 7,832,875 B2 | 11/2010 | Matic-Vujovic et al. | |
| 8,758,802 B2 | 6/2014 | Muthukumar et al. | |
| 9,061,050 B2 | 6/2015 | Gobin et al. | |
| 9,675,589 B2 * | 6/2017 | Muthukumar | A61K 31/765 |

(Continued)

FOREIGN PATENT DOCUMENTS

| | | |
|---|---|---|
| CA | 1269327 A | 5/1990 |
| CN | 1093259 A | 10/1994 |

(Continued)

OTHER PUBLICATIONS

Margalit et al., Retina 20, 469-77 (2000).*
Liu et al., J. Chromatogr. A 1046, 121-26 (2004).*
Thompson, et al., "Synthesis and applications of heterobifunctional poly(ethylene oxide) oligomers," Polymer, 49(2), Jan. 21, 2008, pp. 345-373. (Year: 2008).*
CN 1471924 A; published Feb. 4, 2004; Abstract only; 2 pages.
IN208748 A1, May 5, 2007, "Composition for Treatment of Cataract"; Rpendra et al.; English Abstract only; 1 page.
International Search Report and Written Opinion; International Application No. PCT/US2014/027852; International Filing Date Mar. 14, 2014; dated Jul. 2, 2014; 12 pages.
JP02-258727, published Oct. 19, 1990; Liposome Pharmaceutical Containing Gamma-L-Glutamyl-L-Cysteine Ester Derivative; from JP Office Action for Application P2012-543328; dated Aug. 26, 2014, Abstract only.

(Continued)

*Primary Examiner* — Theodore R. West
(74) *Attorney, Agent, or Firm* — Cantor Colburn LLP

(57) ABSTRACT

Described herein are methods of inhibiting or reversing the progression of cataract formation or presbyopia in an eye by administering a γ-crystallin charge masking agent. Both presbyopia and cataracts are caused by aggregation of the soluble crystalline lens proteins called the crystallins.

12 Claims, 9 Drawing Sheets

(56) References Cited

U.S. PATENT DOCUMENTS

| | | | |
|---|---|---|---|
| 9,789,091 B2* | 10/2017 | Muthukumar | A61K 31/765 |
| 2003/0130324 A1 | 7/2003 | McAvoy et al. | |
| 2003/0223957 A1* | 12/2003 | Schwartz | A61K 9/0048 424/78.38 |
| 2004/0038294 A1 | 2/2004 | Evangelista et al. | |
| 2004/0043082 A1 | 3/2004 | Karageozian et al. | |
| 2004/0120967 A1 | 6/2004 | Calvani | |
| 2004/0254197 A1 | 12/2004 | Tasaka et al. | |
| 2005/0079197 A1 | 4/2005 | Kataoka et al. | |
| 2005/0249821 A1 | 11/2005 | Paul, Jr. | |
| 2005/0260259 A1 | 11/2005 | Bolotin | |
| 2006/0147415 A1 | 7/2006 | Mousa et al. | |
| 2007/0275098 A1 | 11/2007 | Banks | |
| 2008/0094573 A1 | 4/2008 | Vermette et al. | |
| 2008/0227700 A1 | 9/2008 | Ghosh et al. | |
| 2009/0247604 A1 | 10/2009 | Tang et al. | |
| 2009/0324691 A1 | 12/2009 | Mahadevan et al. | |
| 2010/0210531 A1 | 8/2010 | Johnson et al. | |
| 2010/0226963 A1* | 9/2010 | Cooper | A61K 9/0043 424/429 |
| 2014/0274962 A1 | 9/2014 | Muthukumar et al. | |
| 2014/0315800 A1 | 10/2014 | Ochiai et al. | |
| 2015/0010634 A1 | 1/2015 | Knappe et al. | |
| 2015/0157721 A1 | 6/2015 | Wu | |
| 2015/0297740 A1 | 10/2015 | Rau et al. | |
| 2016/0000707 A1 | 1/2016 | Muthukumar et al. | |
| 2016/0074370 A1 | 3/2016 | Muthukumar et al. | |
| 2017/0135972 A1 | 5/2017 | Muthukumas | |

FOREIGN PATENT DOCUMENTS

| | | |
|---|---|---|
| CN | 1621091 | 6/2005 |
| CN | 1660920 | 8/2005 |
| CN | 102172410 | 9/2011 |
| CN | 102579353 A | 7/2012 |
| DE | 3906311 A1 | 8/1990 |
| EP | 0641563 A1 | 3/1995 |
| JP | 2004161731 | 6/2004 |
| KR | 2010000203 | 1/2010 |
| WO | 199200748 A1 | 1/1992 |
| WO | 199300109 A1 | 1/1993 |
| WO | 9416648 | 8/1994 |
| WO | 9514482 A1 | 6/1995 |
| WO | 199514482 A1 | 6/1995 |
| WO | 199524899 A1 | 9/1995 |
| WO | 2000071723 A2 | 11/2000 |
| WO | 0191775 | 12/2001 |
| WO | 200191775 A3 | 12/2001 |
| WO | 200248190 A1 | 6/2002 |
| WO | 2003003073 A1 | 1/2003 |
| WO | 2005117987 A1 | 12/2005 |
| WO | 2007025763 A2 | 3/2007 |
| WO | 2008145721 A2 | 12/2008 |
| WO | 2009051223 A1 | 4/2009 |
| WO | 2010007626 A1 | 1/2010 |
| WO | 2010065024 A1 | 6/2010 |
| WO | 2010130638 A1 | 11/2010 |
| WO | 2011075430 A1 | 6/2011 |
| WO | 2012059882 A2 | 5/2012 |
| WO | 2012109975 A1 | 8/2012 |
| WO | 2012135682 A2 | 10/2012 |
| WO | 2012142659 A1 | 10/2012 |
| WO | 2012167081 A1 | 12/2012 |
| WO | 2014071132 A1 | 5/2014 |
| WO | 2014152818 A1 | 9/2014 |
| WO | 2014171842 A1 | 10/2014 |

OTHER PUBLICATIONS

PEGylation Reagents (linkers, crosslinkers and labels)_Products Description; by Uptima; uptima@interchim.com; printer Nov. 30, 2012; 12 pages.

PH Value Eye Drops, A Not Too Scientific Description of pH Value Eye Drops, Aug. 22, 2014.

Qian, et al.; "Effects of Anionic Surfactant SDS on the Photophysical Properties of Two Fluorescent Molecular Sensors"; Journal of Photochemistry and Photobiology A: Chemistry 200; pp. 402-409; (2008).

Wang et al.; "Safety and Efficacy of Intracapsular Tranilast Microspheres in Experimental Posterior Capsule Opacification"; Journal Cataract and Refractive Surgery; 33; pp. 2122-2128; (2007).

Wang et al.; "Treatment with mPEG-SPA Improves the Survival of Corneal Grafts in Rats by Immune Camouflage"; Biomaterials; 43; pp. 13-22p (2015).

"Secondary Cataracts: Cloudy Vision Cleared With Laser Treatment"; from Pacific Cataract and Laser Institute; www.pcli.com; copyright 2011; printed Apr. 28, 2017; 2 pages.

* cited by examiner

METHODS OF INHIBITING CATARACTS AND PRESBYOPIA

CROSS-REFERENCE TO RELATED APPLICATIONS

This application is a Continuation of U.S. application Ser. No. 14/943,471, filed on Nov. 17, 2015, which is a Continuation of U.S. application Ser. No. 14/772,254 filed on Sep. 2, 2015, which is a 371 of PCT/US2014/027852, filed on Mar. 14, 2014, which claims the benefit of priority to U.S. provisional application No. 61/782,860, filed on Mar. 14, 2013, under the provisions of 35 U.S.C. 119 and the International Convention for the protection of Industrial Property, which are incorporated herein by reference.

FIELD OF THE DISCLOSURE

The present disclosure relates to methods of inhibiting or reversing the progression of age related changes in the crystalline lens of an eye.

BACKGROUND

The crystalline lens of the eye is a transparent structure that is suspended immediately behind the iris, which brings rays of light to a focus on the retina. The lens contains both soluble and insoluble proteins; together they constitute 35 percent of the wet weight of the lens. In a young, healthy lens, the soluble proteins, commonly referred to as crystallins, constitute 90 percent of the lens proteins. During the aging process, the lens crystallins form insoluble aggregates, which, at least in part, account for the decreased deformability of the lens nucleus, which characterizes presbyopia, the loss of the eye's ability to change focus to see near objects. The formation of insoluble aggregates of lens crystallins in presbyopia is believed to be an early stage in the formation of age-related cataracts.

Cataracts are defined by cloudiness or opacification in the crystalline lens of the eye. As an individual ages, cataracts form as the crystallins present in the lens are converted into aggregates, resulting in increased lens opacity. Specifically, there is a progressive decrease in the concentration of the soluble chaperone, α-crystallin, in human lens nuclei with age, as it becomes incorporated into high molecular weight aggregates and insoluble protein. The presence of aggregates compromises the health and function of the lens and left untreated, cataracts can lead to substantial vision loss or even blindness. Presently, the most common treatment for cataracts is surgery.

Crystallins are structural proteins most highly expressed in the lens fiber cells of the vertebrate eye. The crystallins are divided into two subfamilies: the α-crystallins (αA and αβ) which are members of the small heat shock protein superfamily, also functioning as structural proteins and molecular chaperones; and the evolutionarily-linked superfamily of β- and γ-crystallins which function primarily as structural proteins in the lens, and contribute to the transparency and refractive properties of lens structure. In addition to their role in cataract development, αA-crystallin and αB-crystallin have been implicated in neurodegenerative diseases, like Alexander's disease, Creutzfeldt-Jacob disease, Alzheimer's disease and Parkinson's disease.

U.S. Patent Application 2008/0227700 describes deaggregation of proteins using peptides having chaperone activities as a therapeutic treatment. Specifically, αB peptides were used to deaggregate pH-induced aggregates of β-crystallin as measured by light scattering. Provision of a continuous supply of alpha crystallins into the lens is a challenge. What is needed are alternative methods suitable for the deaggregation of crystallins for the inhibition and/or reversal of cataracts and presbyopia.

SUMMARY

In one aspect, a method of inhibiting or reversing the progression of cataract formation or presbyopia in an eye comprises contacting the eye with an effective cataract or presbyopia-inhibiting amount of an ophthalmic composition comprising at least one γ-crystallin charge masking agent, wherein the charge masking agent is not a polypeptide.

In another aspect, an ophthalmic composition comprises a bifunctional molecule containing a leaving group covalently linked to a molecular bristle.

In another aspect, a method of inhibiting or reversing the progression of age related degeneration of a crystalline lens in an eye comprises contacting the eye with an effective degeneration-inhibiting amount of an ophthalmic composition comprising at least one γ-crystallin charge masking agent, wherein the γ-crystallin charge masking agent is not a polypeptide.

In yet another aspect, a method of treating a disease relating to protein folding in a patient in need thereof comprises administering a therapeutically effective amount of a bifunctional molecule containing a leaving group covalently linked to a molecular bristle.

BRIEF DESCRIPTION OF THE DRAWINGS

FIG. 1 shows MALDI-TOF data for modification of γ-crystallin with PEG24.

FIG. 2 shows the NICF of γ-crystallin modified with PEG24.

FIG. 3 shows the distribution function of γ-crystallin modified with PEG24.

FIG. 4 shows the graph of Γ versus $q^2$ for γ-crystallin modified with PEG24.

FIG. 5 shows MALDI-TOF data for modification of γ-crystallin with PEG4.

FIG. 6 shows the NICF of γ-crystallin modified with PEG4.

FIG. 7 shows the distribution function of γ-crystallin modified with PEG4.

FIG. 8 shows the graph of Γ versus $q^2$ for γ-crystallin modified with PEG4.

FIG. 9 shows MALDI-TOF data for modification of γ-crystallin with CAPEG.

FIG. 10 shows the NICF of γ-crystallin modified with CAPEG4.

FIG. 11 shows the distribution function of γ-crystallin modified with CAPEG4.

FIG. 12 shows the graph of Γ versus $q^2$ for γ-crystallin modified with CAPEG4.

FIG. 13 shows the distribution function of γ-crystallin modified with MMPEG.

FIG. 14 shows the distribution function of γ-crystallin modified with Biotin.

FIG. 15 shows the distribution function of γ-crystallin modified with Biotin-PEG.

FIG. 16 shows the distribution function of γ-crystallin modified with sulfo-N-hydroxysuccinimide acetate.

Figure 1:
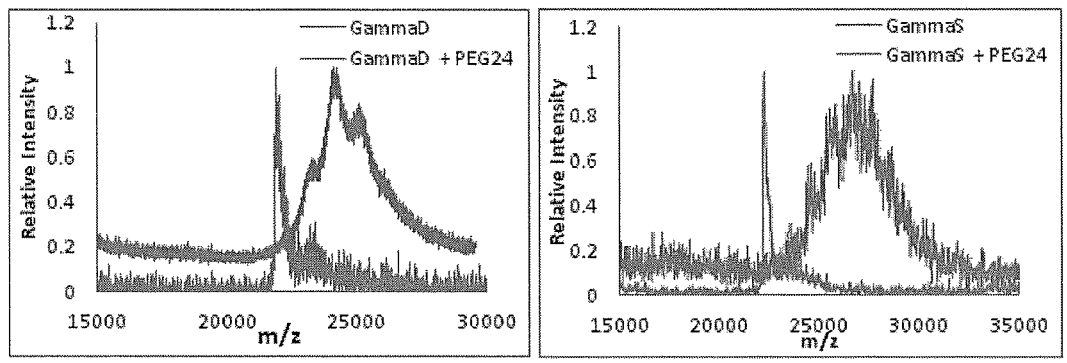

The above-described and other features will be appreciated and understood by those skilled in the art from the following detailed description, drawings, and appended claims.

DETAILED DESCRIPTION

Disclosed herein are methods of disaggregating/preventing formation of a γ-crystallin aggregate comprising contacting the γ-crystallin aggregate with a composition comprising a γ-crystallin charge masking agent in an amount sufficient to disaggregate and/or prevent formation of the γ-crystallin aggregate. One of ordinary skill in the art would recognize that while the molecules disclosed herein are described as a γ-crystallin charge masking agents they may also disaggregate/prevent protein aggregation of β-crystallin as well. Further disclosed are methods of inhibiting or reversing the progression of cataract formation in an eye which comprises contacting the eye with an effective cataract-inhibiting amount of an ophthalmic composition comprising a γ-crystallin charge masking agent. Also disclosed are methods of inhibiting or reversing the progression of presbyopia in an eye which comprises contacting the eye with an effective presbyopia-inhibiting amount of an ophthalmic composition comprising a γ-crystallin charge masking agent. In specific embodiments, the γ-crystallin charge masking agent is not a polypeptide.

The inventors herein have employed techniques such as dynamic light scattering to study the aggregates formed by γ-crystallins in solution. Both the β and γ-crystallins are highly stable structural proteins comprising four Greek-key motifs in two domains. While the β-crystallins form dimers as well as hetero- and homo-oligomers, the γ-crystallins are monomers in the eye. Further, while the β-crystallins exhibit a repulsive force in solution, the γ-crystallins exhibit an attractive interaction attributed to nonspecific protein or water interactions. It has also been hypothesized that thiol modifications cause aggregates of γ-crystallin to form in solution.

The human γ-crystallin family contains five members, the γA-D crystallins and γ-S crystalline. The γA-D crystallins are expressed early in development and are primarily found in the lens core; γC and γD-crystallin are most prevalent. Unfolding and refolding of γ-D crystalline in vitro has been shown to lead to increased protein aggregation due to the lack of stability of the refolded protein γS-crystalline has been shown to be a key protein in the suppression of aggregation of other crystalline proteins, leading to a clear lens.

Without being held to theory, it is believed that the aggregation of γ-crystallin is both an electrostatic and hydrophobic phenomenon, with the electrostatic forces dominating. Adding the heat shock proteins αA- and αB-crystallin disrupts γ-crystallin aggregation. A γ-crystallin charge masking agent that can disrupt electrostatic interactions can substitute for the chaperone activity of α-crystallin and prevent/reduce γ-crystallin aggregate size.

Treatment with γ-crystallin charge masking agents can be used to treat diseases and/or conditions resulting from aggregation of γ-crystallins such as cataracts and presbyopia. As used herein, a cataract is an opacity of the crystalline lens of the eye caused by altered protein interactions in the lens. Protein interactions include misfolding of proteins as well as protein-protein interactions such as aggregation. Presbyopia is the impairment of vision due to advancing years or old age. Symptoms of presbyopia include decreased focusing ability for near objects, eyestrain, difficulty reading fine print, fatigue while reading or looking at an illuminated screen, difficulty seeing clearly up close, less contrast when reading print, need for brighter and more direct light for reading, needing to hold reading material further away in order to see it clearly, and headaches, especially headaches when using near vision. Individuals suffering from presbyopia may have normal vision, but the ability to focus on near objects is at least partially lost over time, and those individuals come to need glasses for tasks requiring near vision, such as reading. Presbyopia affects almost all individuals over the age of 40 to a greater or lesser degree.

In the method of inhibiting the progression of cataract formation in an eye, the eye may already contain one or more developing or fully developed cataracts before it is contacted with the γ-crystallin charge masking agent. Accordingly, the method can be used to inhibit the formation of further cataracts in the eye, or to inhibit the formation of mature cataracts from the developing cataracts already present in the eye. Alternatively, the eye may be free of any developing or fully developed cataracts before it is contacted with the γ-crystallin charge masking agent.

In the method of reversing the progression of cataract formation in an eye, at least partial to full reversal of cataracts in the eye is achieved by contacting the eye with a γ-crystallin charge masking agent as disclosed herein.

Similarly, in the method of inhibiting the progression of presbyopia in an eye, the individual may already be experiencing one or more symptoms of presbyopia before the eye is contacted with the γ-crystallin charge masking agent. Accordingly, the method can be used to reduce the progression of the symptom(s) experienced, or to inhibit the formation of additional symptoms of presbyopia. Alternatively, the eye may be free of any symptoms of presbyopia before it is contacted with the γ-crystallin charge masking agent.

In the method of reversing the progression of presbyopia in an eye, at least partial to full reversal of the symptoms of presbyopia in the eye is achieved by contacting the eye with a γ-crystallin charge masking agent as disclosed herein.

As used herein, γ-crystallin charge masking agent is a molecule suitable to interfere with γ-crystallin electrostatic protein-protein interactions which lead to γ-crystallin aggregation. In one embodiment, the masking agent is not a polypeptide. γ-crystallin charge masking agents prevent γ-crystallin aggregates from forming and/or reduce the size of pre-formed aggregates.

In one embodiment, the γ-crystallin charge masking agent is a high concentration salt solution, having a salt concentration over 400 mM. The term "salt" as used herein, is intended to include an organic or inorganic salt, including but not limited to one or more of NaCl, KCl, ammonium halides such as $NH_4Cl$, alkaline earth metal halides such as $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof. Additional organic salts include alkylammonium salts such as ethylammonium nitrate, sodium citrate, sodium formate, sodium ascorbate, magnesium gluconate, sodium gluconate, trimethamine hydrochloride, sodium succinate, and combinations thereof. Without being held to theory, it is believed that the identity of the ion, e.g., Li+, Na+ and K+, can affect the ability of the γ-crystallin charge masking agent to prevent γ-crystallin aggregation.

It was unexpectedly shown herein that salt, e.g. KCl, concentrations of less than 300 nM did not provide a reduction in the size of γ-crystallin aggregates. However, at KCl concentrations to 400 to 1000 mM, aggregate formation was effectively inhibited.

In another embodiment, the γ-crystallin charge masking agent is a bifunctional molecule containing a leaving group covalently linked to a molecular bristle. The bifunctional molecule interacts with charges on the γ-crystallin molecules, such as positively charged lysine and arginine residues and negatively charged glutamate and aspartate residues. The molecular bristle is a hydrophilic, water-soluble species that provides distance between the γ-crystallin molecules, preventing aggregation. Without being held to theory, it is believed that the bifunctional molecule reacts and effectively puts the molecular bristle onto the protein, and the leaving group is expelled during the reaction. The covalently attached molecular bristle prevents aggregation of the γ-crystallin molecules. Without being held to theory, it is believed that the bifunctional molecules described herein may also act as β-crystallin interaction inhibitors.

Figure 17:
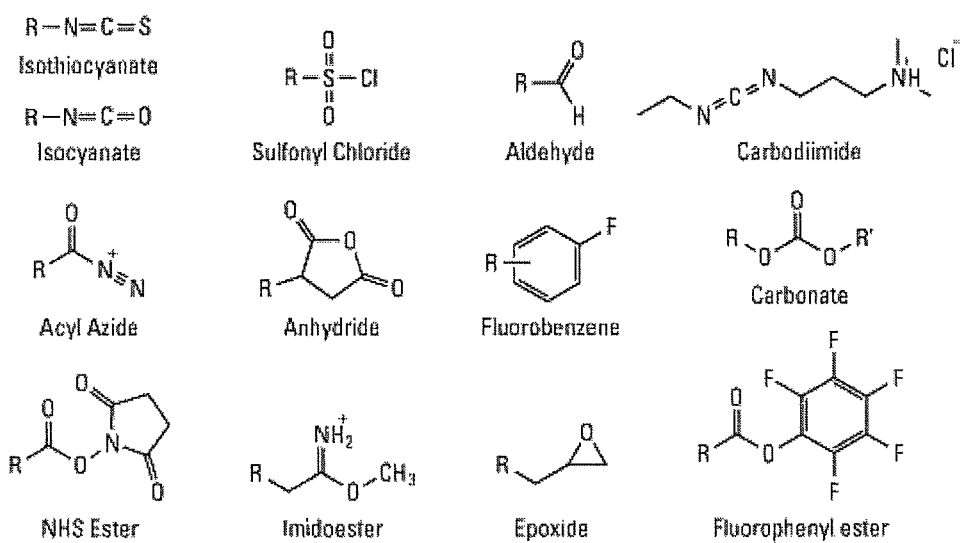
FIG. 17 shows embodiments of charge masking groups. In each structure, R is the molecular bristle.

Exemplary leaving groups (also called reactive groups) include succinimide and carboxylic acid functional groups, specifically N-hydroxysuccinimide and COOH. In some embodiments, the leaving group is biocompatible. Other examples of leaving groups include isocyanate, isothiocyanate, sulfonyl chloride, aldehyde, carbodiimide, acyl azide, anhydride, fluorobenzene, carbonate, N-hydroxysuccinimide ester, imidoester, epoxide, and fluorophenyl ester. FIG. 17 shows embodiments of leaving groups wherein the R group is the molecular bristle. When the bifunctional molecule contains COOH, water leaves when it reacts with a protein's amine group. When the bifunctional molecule contains N-hydroxysuccinimide water is not released. In an NH$_2$ reaction, water leaves when NH$_2$ reacts with a COOH group on the protein.

Figure 18:
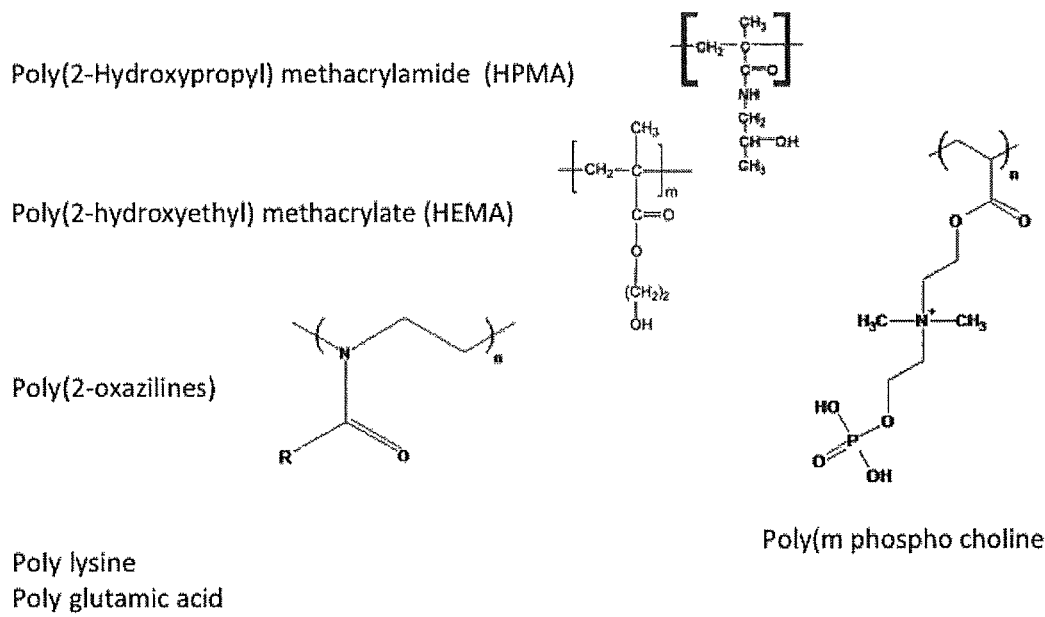
FIG. 18 shows embodiments of molecular bristles.

Exemplary molecular bristles include linear or branched polyethylene glycols having 4 or more oxyethylene groups, such as 4 to 200 oxyethylene groups. Also included are modified polyethylene glycols such as alkoxy- and aryloxy polyethylene glycols having 4 to 200, specifically 4 to 24 oxyethylene, alkloxy ethylene or aryloxy ethylene groups. Alternative molecular bristles include poly(2-hydroxypropyl)methacrylamide (HPMA), poly(2-hydroxyethyl)methacrylate (HEMA), poly(2-oxazilines), poly(m-phosphocholine), poly lysine, and poly glutamic acid. FIG. 18 shows embodiments of molecular bristles. In one embodiment, the molecular bristle has a number average molecular weight of 150 to 8000.

In a specific embodiment, the bifunctional γ-crystallin charge masking agent is:

or

In one embodiment, the bifunctional γ-crystallin charge masking agents described herein are also useful in the treatment of diseases relating to protein folding such as Alzheimer's disease, Parkinson's disease, and Huntington's disease. In a specific embodiment, the bifunctional γ-crystallin charge masking agents are administered as oral compositions.

In one embodiment, the γ-crystallin charge masking agent is not a polypeptide. "Polypeptide", "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

An advantage of the γ-crystallin charge masking agents described herein is that they are expected to be effective in the presence of post-translational modifications of γ-crystallins, including, for example, transamidation, oxidation, modified and dysfunctional connexins, and high concentrations of inorganic and organic ions such as Ca$^{+2}$.

The γ-crystallin charge masking agents are contacted with the eye to inhibit the progression of cataracts and/or reduce existing cataracts, or to inhibit and/or reduce the symptoms of presbyopia. As used herein, the term "contacting the eye" encompasses methods of directly applying the γ-crystallin charge masking agent to the eye. In the above-described method, suitable means known to those of ordinary skill in the art may be used to contact the eye with the compound. Examples of such methods include, but are not limited to, the compound being injected into the eye, being dropped or sprayed into the eye, applied in the form of an ophthalmic device, applied by iontophoresis, or otherwise topically applied to the eye.

As used herein, the term "effective cataract-inhibiting amount" means an amount which will inhibit the progression or formation of cataracts in an eye or inhibit the progression or formation of mature cataracts from developing cataracts already present in the eye. The effective cataract-inhibiting amount of the γ-crystallin charge masking agent will depend on various factors known to those of ordinary skill in the art. Such factors include, but are not limited to, the size of the eye, the number and progression of any fully developed or developing cataracts already present in the eye, and the mode of administration. The effective cataract-inhibiting amount will also depend on whether the pharmaceutical composition is to be administered a single time, or whether the pharmaceutical composition is to be administered periodically, over a period of time. The period of time may be any number of days, weeks, months, or years. In one embodiment, the effective cataract-inhibiting amount of the γ-crystallin charge masking agent, specifically the bifunctional molecules described herein, is about 0.001 g to about 0.1 g. Specifically, the effective cataract-inhibiting amount is about 0.01 g to about 0.05 g.

As used herein, the term "effective presbyopia-inhibiting amount" means an amount which will reduce a symptom of presbyopia in an eye or inhibit the progression of additional symptoms of presbyopia in the eye. The effective presbyopia-inhibiting amount of the γ-crystallin charge masking agent will depend on various factors known to those of ordinary skill in the art. Such factors include, but are not limited to, the size of the eye, the number and type of symptoms already present in the individual, and the mode of administration. The effective cataract-inhibiting amount will also depend on whether the pharmaceutical composition is to be administered a single time, or whether the pharmaceutical composition is to be administered periodically, over a period of time. The period of time may be any number of days, weeks, months, or years. In one embodiment, the effective presbyopia-inhibiting amount of the γ-crystallin charge masking agent, specifically the bifunctional molecules described herein, is about 0.001 g to about 0.1 g. Specifically, the effective presbyopia-inhibiting amount is about 0.01 g to about 0.05 g.

As used herein the term "ophthalmic composition" refers to a pharmaceutically acceptable formulation, delivery device, mechanism or system suitable for administration to the eye. The term "ophthalmic compositions" includes but are not limited to solutions, suspensions, gels, ointments, sprays, depot devices or any other type of formulation, device or mechanism suitable for short term or long term delivery of $β_L$-crystallin electrostatic interaction inhibitors to the eye. In contrast to oral formulations, for example, ophthalmic compositions exhibit specific technical characteristics associated with their application to the eyes, including the use of pharmaceutically acceptable ophthalmic vehicles that avoid inducing various reactions such as, for example, irritation of the conjunctiva and cornea, closure of the eyelids, secretion of tears and painful reactions. Specific ophthalmic compositions are advantageously in the form of ophthalmic solutions or suspensions (i.e., eye drops), ophthalmic ointments, or ophthalmic gels containing $β_L$-crystallin electrostatic interaction inhibitors. Depending upon the particular form selected, the compositions may contain various additives such as buffering agents, isotonizing agents, solubilizers, preservatives, viscosity-increasing agents, chelating agents, antioxidizing agents, antibiotics, sugars, and pH regulators.

Examples of preservatives include, but are not limited to chlorobutanol, sodium dehydroacetate, benzalkonium chloride, pyridinium chlorides, phenethyl alcohols, parahydroxybenzoic acid esters, benzethonium chloride, hydrophilic dihalogenated copolymers of ethylene oxide and dimethyl ethylene-imine, mixtures thereof, and the like. The viscosity-increasing agents may be selected, for example, from methylcellulose, hydroxyethylcellulose, carboxymethylcellulose, hydroxypropylmethylcellulose, polyvinyl alcohol, carboxymethylcellulose, chondroitin sulfate, and salts thereof. Suitable solubilizers include, but are not limited to, polyoxyethylene hydrogenated castor oil, polyethylene glycol, polysorbate 80, and polyoxyethylene monostearate. Typical chelating agents include, but are not limited to, sodium edetate, citric acid, salts of diethylenetriamine pentaacetic acid, diethylenetriamine pentamethylenephosphonic acid, and stabilizing agents such as sodium edetate and sodium hydrogen sulfite.

Exemplary buffers include, but are not limited to borate buffers, phosphate buffers, carbonate buffers, acetate buffers and the like. The concentration of buffer in the ophthalmic compositions may vary from about 1 mM to about 150 mM or more, depending on the particular buffer chosen.

As used herein, the term "vehicle" is intended to include a carrier, diluent or excipient suitable for ophthalmic use. "Excipient" refers to an ingredient that provides one or more of bulk, imparts satisfactory processing characteristics, helps control the dissolution rate, and otherwise gives additional desirable characteristics to the compositions. In particular, the excipients are selected such that the ophthalmic composition does not trigger a secretion of tears that will entrain the active ingredient. Acceptable excipients are well known to a person skilled in the art, who will know how to select them depending on the desired formulation.

In one embodiment, the γ-crystallin charge masking agent is administered in the form of an ophthalmic device, such as a contact lens or a punctal plug. Suitable ophthalmic devices included biocompatible devices with a corrective, cosmetic or therapeutic quality.

In one embodiment, the γ-crystallin charge masking agent may be adhered to, incorporated into or associated with a contact lens, optionally as a controlled-release composition. The contact lens may be produced using the known materials, for example hydrogels, silicone hydrogels, silicone elastomers and gas permeable materials such as polymethylmethacrylate (PMMA), methacrylic acid ester polymers, copolymers of oligosiloxanylalkyl(meth)acrylate monomers/methacrylic acid and the like. Specific examples of materials for water-containing soft ophthalmic lenses include those described in U.S. Pat. No. 5,817,726, 2-hydroxyethyl methacrylate polymers as described in U.S. Pat. No. 5,905,125, ophthalmic lens materials as described in European Patent Application No. 781,777, the hydrogel lens which is coated with a lipid layer in advance as described in U.S. Pat. No. 5,942,558; all incorporated herein for their teachings regarding contact lenses. Generally used contact lens such as hard or rigid cornea-type lens, and gel, hydrogel or soft-type lens which are produced from the above known materials may be used.

It is common in the contact lens industry to characterize contact lenses into two major categories; conventional and silicone hydrogels. The conventional based hydrogels started as poly(hydroxyethyl methacrylate) (poly HEMA) and evolved to polyHEMA copolymers with other hydrophilic moieties such as n-vinyl pyrrolidone (nVP), acrylamide, dimethyl acrylamide, and methacrylated phosphorylcholines. Polyvinyl alcohol lenses may also be employed.

The silicone hydrogels (SiH) typically consist of copolymers of methacrylated or meth(acrylamide) silicone monomers, prepolymers or macromers with typical conventional hydrogel monomers. Examples of silicone monomers include "Tris", alkyl terminated, methacrylated polydimethylsiloxane (PDMS), and block copolymers of silicone and hydrophilic monomers. ABA triblock copolymers are common where the A group is a hydrophilic block and the B group is the silicone monomer block. In addition to the methacrylates, other reactive groups include vinyl, acrylamide, or any other reactive group capable of chain reaction polymerization. Crosslinking and polymerization can also be achieved via step-growth polymerization using monomers with bi-functionality. An example is the reaction of a hydroxyl group with a carboxylic acid group in two amino acids or from terepthalic acid and ethylene glycol.

Plasma based coating methods are commonly used on silicone hydrogels including plasma oxidation and plasma coatings.

A sustained-release γ-crystallin charge masking agent composition may be produced, for example, by incorporating in, associating with or adhering to the contact lens the γ-crystallin charge masking agent composition according to the known methods for producing the contact lenses with sustained-release drugs as described in U.S. Pat. Nos. 5,658, 592; 6,027,745; WO2003/003073; US-2005-0079197, incorporated herein for their teachings regarding contact lenses and sustained release. Specifically, the contact lens may be produced by adhering the γ-crystallin charge masking agent to a part of a finely-divided or gel sustained-releasing agent such as polyvinyl pyrrolidone, sodium hyaluronate and the like. In addition, sustained release may be produced by forming a γ-crystallin charge masking agent composition reservoir such as by producing a contact lens from a member which forms a front surface of the lens and a member which forms a rear surface of the lens.

In one embodiment the charge masking agent may be inserted into the aqueous or vitreous as an injection with controlled release.

In one embodiment, the γ-crystallin charge masking agent is administered in a punctal plug. As used herein, the term punctal plug refers to a device of a size and shape suitable for insertion into the inferior or superior lacrimal canaliculus of the eye through, respectively, the inferior or superior lacrimal punctum.

In one embodiment, the γ-crystallin charge masking agent is administered by iontophoresis. Iontophoresis is a technique using a small electric charge to deliver a medicine or other chemical through the skin.

In one embodiment, the ophthalmic composition is administered using ultrasound enhancement.

The invention is further illustrated by the following non-limiting examples.

EXAMPLES

Example 1: Cloning of γ-Crystallin

The γD- and γS-crystallin DNA sequences are in pQe1 plasmids that were provided by the King Labs at Massachusetts Institute of Technology (Cambridge, Mass.). γ-crystallin protein sequences contain a 6× N-terminal histidine tag (his tag) for purification purposes. The plasmids were transformed into a cloning competent cell line to create additional plasmid DNA. Plasmids were subsequently transformed into an expression competent cell line for protein synthesis (TAM 1 E. coli cells (Active Motif. Carlsbad, Calif.)).

γ-crystallin plasmid DNA was chemically transformed into M15pRep E. coli cells for protein synthesis. 1 L cultures were grown for protein purification. γ-crystallin protein was purified by Ni affinity chromatography. The N-terminal His tag contained on the γ-crystallin proteins preferentially binds to the Ni column. The bound protein can be eluted with an imidazole gradient which competitively binds to the Ni, releasing the purified protein. Purity was confirmed by SDS PAGE gel electrophoresis and fast protein liquid chromatography (FPLC).

Example 2: Effect of pH and Salt on Purified γD- and γS-Crystallin

Because pH and salt have an effect on the aggregation of β-crystallin, the effect of pH and salt on γ-crystallin was also studied. Particle sizes were measured using dynamic light scattering (DLS).

Experimental dynamic light scattering (DLS) was measured using an ALV goniometer instrument which had an ALV-5000/E correlator equipped with 288 channels (ALV, Langen Germany) and a 2 W argon laser (Coherent Inc., Santa Clara, Calif.), with a working power of approximately 40 mW. Scattering intensity was measured at angles between 30° and 90° at 5° intervals, corresponding to a scattering wave vector (q) range between $8.41 \times 10^6$ and $2.30 \times 10^7$ m$^{-1}$. The scattering wave vector is defined as $q = 4\pi n \sin(\theta/2)/\lambda$, where θ is the scattering angle, and λ=514.5, the wavelength of the argon laser in vacuum, and n is 1.33, the refractive index of water. The temperature of the sample was held at constant temperature of 4 to 37±0.1° C. by a circulating water bath.

The correlation function was analyzed using CONTIN analysis to calculate lag times for the correlation functions at measured angles. The peaks represent the diffusive mode of the proteins. The delay times (τ) were converted to Γ and graphed versus $q^2$. The slope of the fitted line is the diffusion coefficient (D). The lines are fitted such that the intercept is zero because a non-zero value of q=0 is unphysical. The Γ versus $q^2$ plots were linear with $r^2$ values of 0.95 or greater.

DLS measurements were performed on both modified and unmodified γD- and γS-crystallin proteins at 150 mM NaCl, 20 mM $Na_2HPO_4/NaH_2PO_4$ buffer pH 6.8 at a concentration of 0.5 mg/mL. All solutions were filtered with 0.22 μm hydrophobic PVDF membranes (Fisher Scientific) into 10 mm diameter borosilicate glass tubes and sealed. Solutions were allowed to equilibrate for thirty minutes prior to measuring light scattering.

Individual solutions of α-A, α-B, γD- and γ-S crystallin proteins were investigated to understand the size scale and how the proteins behave in dilute solution. (Table 1) Temperature had little effect on protein size in solution as measured by DLS.

TABLE 1

DLS measurements performed on both modified and unmodified γD- and γ-S - crystallin proteins

| Temp (° C.) | αA $R_h$ (nm) | αB $R_h$ (nm) | γD $R_{hf}$ (nm) | γD $R_{hs}$ (nm) | γS $R_{hf}$ (nm) | γS $R_{hs}$ (nm) |
|---|---|---|---|---|---|---|
| 4° | 12 | 12 | 3 | 116 | 3 | 100 |
| 22° | 12 | 13 | 2.8 | 104 | 2.7 | 102 |
| 37° | 13 | 13 | 2.7 | 109 | 2.6 | 95 |

Considering that the molecular weight of αA-crystallin is 19.9 kDa and α-B crystalline is 20.16 kDa, the size seen in the DLS experiment is consistent with α-crystallin's known assembly into 300-1200 kDa species in solution as well as in the human eye.

The 3 nm $R_h$ for the γ-crystallins represents a single protein species which correlates well with the molecular weights of 20.6 kDa and 20.9 kDa for monomeric γD- and γ-S crystallin, respectively. Both species also show aggregates with $R_h$ values of 110 and 100 nm for γD- and γS-crystallins, respectively. Aggregation of γ-crystallin has previously been attributed to the attractive interactions between γ-crystallins. The lack of specific protein-protein interactions in the γ-crystallins allows them to form large aggregates in solution.

γ-crystallins were subjected to a variety of experimental conditions, including a range of pHs (5, 6, 7, 8, 9, 10, 11), concentrations of KCl (100 mM, 150 mM, 300 mM, 500 mM, 1000 mM) and temperature (4.5° C., 22° C., 37° C.). The pH and salt concentration were adjusted via overnight dialysis at 4° C. and their final concentration adjusted to 1.0 g/L.

TABLE 2

Effect of pH and salt on γD- and γ-S crystallin

| | γD | | γS | |
|---|---|---|---|---|
| Variable | Rh_f (nm) | Rh_s (nm) | Rh_f (nm) | Rh_s (nm) |
| 100 mM NaCl | 2.8 | 108 | 2.7 | 104 |
| 150 mM NaCl | 2.8 | 104 | 2.7 | 102 |
| 300 mM NaCl | 2.6 | 91 | 2.9 | 100 |
| 400 mM NaCl | 2.7 | — | 2.6 | — |
| 500 mM NaCl | 2.8 | — | 2.5 | — |
| 1000 mM NaCl | 2.5 | — | 2.6 | — |
| pH 5 | 3.9 | 100 | 4.8 | 141 |
| pH 6 | 2.7 | 118 | 2.5 | 110 |
| pH 8 | 2.9 | 102 | 3.0 | 96 |
| pH 9 | 3.5 | 97 | 2.9 | 106 |
| pH 10 | 3.2 | — | 3.4 | 90 |
| pH 11 | 3.1 | — | 3.1 | — |

As can be seen in Table 2, varying pH above 10 removed the aggregates from γD- and γS-crystallin solutions. Salt concentrations over 300 mm KCl did reduce γ-crystallin aggregates to individual protein particles. These results indicate that the large aggregates of γ-crystallin can be disrupted or prevented by interfering with the electrostatic interactions between the γ-crystallins.

It had been hypothesized that disulfide bonds might mediate the observed γ-crystallin aggregates. The DLS of the γ-crystallin proteins was also measured in 5 mM DTT, and in the presence of 1.0 g/L α-crystallin. As shown in Table 3, DTT had no effect on the size of the γ-crystallin aggregates. Thus, this hypothesis was incorrect.

Further, the synthesized α-crystallin proteins were mixed with γ-crystallin proteins to determine if the chaperoning ability of α-crystallin disrupts the γ-crystallin aggregates. The α-A and α-B crystallins were each individually mixed with γD- or γS-crystallin in a molar ratio of 3:1, respectively, mimicking the ratio found in the human eye lens. All solutions were allowed to equilibrate for an hour at 4° C. Upon incubation with α-A or α-B crystallin, the large γ-crystallin aggregate of several hundred nanometers disappeared and the individual γ-crystallin and α-crystallin macromolecules were seen. (Table 3) These data support previous work demonstrating that the α-crystallins suppress nonspecific protein aggregation thus preventing the aggregation of γ-crystallin proteins.

TABLE 3

Effect of DTT and chaperones on γD- and γ-S crystallin

| | γD | | γS | |
|---|---|---|---|---|
| Additive | Rh_f (nm) | Rh_s (nm) | Rh_f (nm) | Rh_s (nm) |
| — | 2.8 | 104 | 2.7 | 102 |
| 5 mM DTT | 2.6 | 108 | 3 | 102 |
| αA | 2.7 | 16 | 2.8 | 18 |
| αB | 3.2 | 17 | 3 | 19 |

Without being held to theory, it is hypothesized that the increase in size of α-crystallins (from 63-68 nm to 75 nm) is due to the α-crystallin interaction with denatured or misfolded γ-crystallin. It is clear that the addition of α-crystallin prevents or disrupts the large γ-crystallin species from forming in solution and by disrupting electrostatic charges between the γ-crystallins. The α-crystallins are able to disrupt the large aggregates of γ-crystallin that appear at high concentrations of γ-crystallin. Thus, in the absence of α-crystallin, γ-crystallin will form large soluble aggregates through electrostatic forces that can be interrupted at high pH and high salt concentrations.

Materials and Methods for Characterization of Aggregates

Chemical modification of γD- and γS-crystallin was undertaken to modify the aggregation behavior of these proteins. The methods used to characterize the modified γD- and γS-crystalline are Matrix Assisted Laser Desorption Ionization-Time of Flight (MALDI-TOF), circular dichroism, and dynamic light scattering.

Matrix Assisted Laser Desorption Ionization-Time of Flight

Approximately 2 mg of regular or modified γ-crystallin protein was dialyzed overnight into 5 mM tris (hydroxymethyl) aminomethane hydrochloride (Tris HCl) pH 7. The solution was lyophilized (freeze dried) overnight to obtain a dry crystallin protein powder.

Mass spectrometry data were obtained on an Omniflex MALDI-TOF mass spectrometer (Bruker Daltonics, Inc., Billerica Mass.) equipped with a 337 nm nitrogen laser. Samples (2 mg/mL) were mixed (1:1) with a matrix consisting of 0.1% trifluoroacetic acid (TFA), 50% acetonitrile and 3,5-dimethoxy-4-hydroxycinnamic acid. 1 μL of solution was subsequently deposited on a stainless steel target. The instrument was used in linear mode for data acquisition.

Circular Dichroism

Crystallin samples were dialyzed overnight into 10 mM $Na_2HPO_4/NaH_2PO_4$ buffer pH 6.8 and measured at a concentration of 0.5 mg/mL. CD spectra were measured on a Jasco J715 spectropolarimeter at 22° C. using a quartz cell of 1 mm path length. After allowing the sample to equilibrate for five minutes, spectra were obtained in the range of 250 to 195 nm.

Dynamic Light Scattering

Experimental dynamic light scattering (DLS) was measured using an ALV goniometer instrument which had an ALV-5000/E correlator equipped with 288 channels (ALV, Langen Germany) and a 2 W argon laser (Coherent Inc., Santa Clara, Calif.), with a working power of approximately 40 mW. Scattering intensity was measured at angles between 30° and 90° at 5° intervals, corresponding to a scattering wave vector (q) range between $8.41 \times 10^6$ and $2.30 \times 10^7$ m$^{-1}$. The scattering wave vector is defined as $q = 4\pi n \sin(\theta/2)/\lambda$, where θ is the scattering angle, and λ=514.5, the wavelength of the argon laser in vacuum, and n is 1.33, the refractive index of water. The temperature of the sample was held at constant temperature of 4 to 37±0.1° C. by a circulating water bath.

The correlation function was analyzed using CONTIN analysis to calculate lag times for the correlation functions at measured angles. The peaks represent the diffusive mode of the proteins. The delay times (τ) were converted to Γ and graphed versus $q^2$. The slope of the fitted line is the diffusion coefficient (D). The lines are fitted such that the intercept is zero because a non-zero value of q=0 is unphysical. The Γ versus $q^2$ plots were linear with $r^2$ values of 0.95 or greater.

DLS measurements were performed on both modified and unmodified γD- and γS-crystallin proteins at 150 mM NaCl, 20 mM $Na_2HPO_4/NaH_2PO_4$ buffer pH 6.8 at a concentration of 0.5 mg/mL. All solutions were filtered with 0.22 μm hydrophobic PVDF membranes (Fisher Scientific) into 10 mm diameter borosilicate glass tubes and sealed. Solutions were allowed to equilibrate for thirty minutes prior to measuring light scattering.

Example 3—Chemical Modification of γ D- and γ S-Crystalline with PEG24

The first modification of γ-crystallin was done with NHSPEG24. Amino acids containing primary amines, lysine and arginine, can perform a nucleophilic substitution on N-hydroxy succinimide (NHS) functionalized poly(ethylene glycol) (PEG). NHS is an activated ester which accelerates the Sn2 reaction mechanism because it is a good leaving group. The nucleophilic substitution produces a protein modified with PEG or a PEGylated γ-crystallin protein. PEGylation was chosen because modification of proteins with PEG has been shown to increase solubility and not affect the three dimensional structure or properties. In particular, PEG24 was chosen because of its reasonable molecular weight (1100.39) added and spacer arm length (8.82 nm).

NHSPEG24

Modification of γ-crystallin with PEG24 was successful as demonstrated by the large increase in γ-crystallin molecular weight observed in MALDI-TOF. The maximum relative intensity for γ D-crystallin was at 24,148 m/z or 2 PEG24 units while for γ S-crystallin the peak occurred at 26,711 m/z which corresponds to 4 PEG24 units. (FIG. 1) The excess reactant and reaction conditions were sufficient as there was no unmodified γ-crystallin present in solution. The higher resolution MALDI-TOF data of γ D-crystallin shows an additional two distinct peaks at 23,056 m/z and 25,206 m/z corresponding to 1 and 3 PEG24 modifications.

CD spectroscopy demonstrated that both crystallin proteins appear to keep their native state despite modification. γ D-crystallin showed increased peaks and depths which could be attributed to a slight difference in protein concentration. The good fit with experimental data is expected as it has been previously demonstrated that PEGylation does not interfere with a protein's secondary structure. (data not shown)

Figure 2:
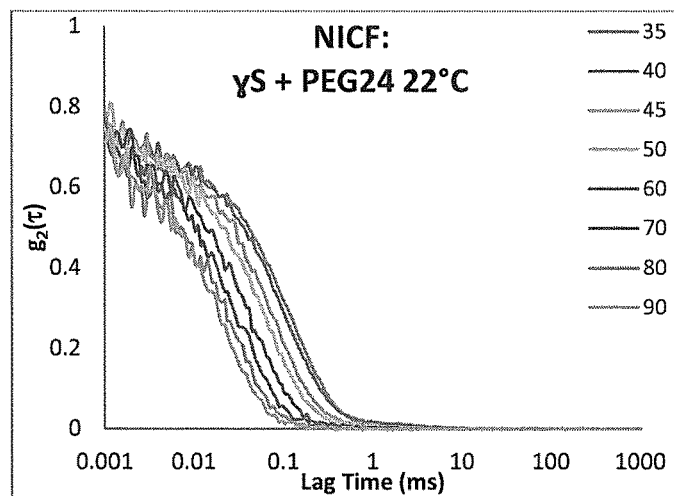
Figure 3:
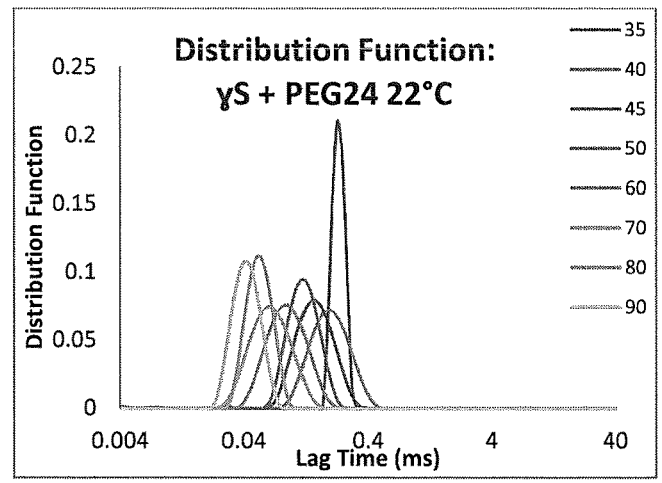
Figure 4:
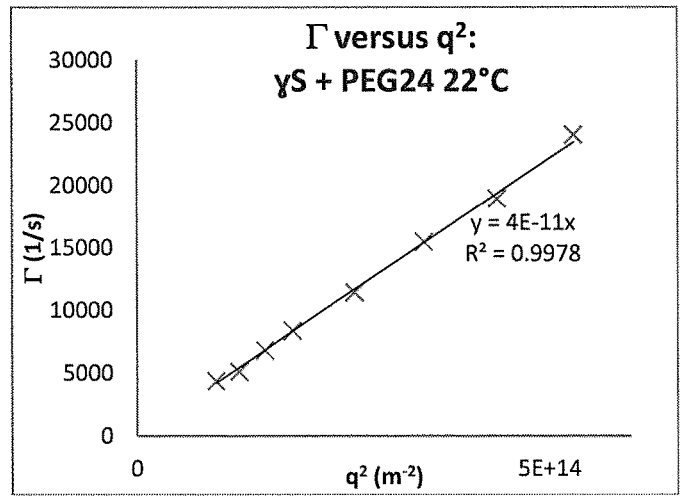

DLS was performed on γ D- and γ S-crystallin modified with PEG24 at 22° C. and 37° C. The NICF provided a distribution function with a single set of peaks which has an angular dependency that can be seen in the graph of Γ versus $q^2$. (FIGS. 2-4) The PEG24 modified γ-crystallin protein had a small size distribution with no additional mode at longer relaxation times which would indicate aggregate formation. For γ D-crystallin, the $R_h$ calculated from the diffusion coefficient was 3.1 nm at 22° and 37° C., while γ S-crystallin had an $R_h$ of 3.2 nm at 22° and 37° C. The $R_h$ values correlated well with the 24.1 kDa and 26.7 kDa molecular weights of γ D- and γ S-crystallin, respectively, measured by MALDI-TOF.

PEGylation of γ-crystallin by NHSPEG24 effectively prevented any aggregation events in dilute solutions as evident in DLS. PEG is a hydrophilic polymer and has been shown to increase the solubility of proteins in solution. Without being held to theory, it is believed that if the aggregation phenomena are a result of solubility issues associated with hydrophobic interactions or electrostatics, then the increased solubility associated with PEGylation prevents the γ-crystallin proteins from aggregation.

Along the same line of thought, without being held to theory, it is believed that the overall surface charge of the proteins has been altered by the reaction with PEG. At a protein's isoelectric point, there is a decrease in solubility which results from the charge neutrality associated with the isoelectric point. Amino acids containing primary amines were the target sites for this type of modification. The primary amine of lysine and arginine can have a positive charge associated with it depending on the protein makeup and solution conditions. By having NHSPEG react onto the lysine and arginine groups the potentially charged sites were occupied by the hydrophilic PEG, thereby changing the protein surface charge. If the aggregation event is a result of electrostatic interactions or a result of the proteins proximity to the isoelectric point then this rational would explain why the aggregate is absent from solution. Modification of γ-crystallin protein with PEG via other reaction mechanisms will be used to examine this possibility.

Without being held to theory, a final explanation for the lack of aggregates in solution is a spacer issue. In the field of hard spherical colloids it has been established that the addition of spacer molecules can reduce aggregation. Adding the PEG24 moiety to γ-crystallin provides a hydrophilic spacer molecule on the surface of the protein. The spacing between proteins provided by PEG could be all that is needed to prevent aggregation of γ-crystallin protein.

Example 4—Chemical Modification of γ D- and γ S-Crystalline with PEG4

γ-crystallin proteins were modified with PEG4 to investigate the effect of spacer arm length on γ-crystallin protein aggregation. The reaction was again performed with NHS functionalized PEG (NHSPEG4) to keep the method of modification the same. PEG4 has a molecular weight added of 219.33 g/mol and spacer arm of 1.6 nm, both of which are smaller than PEG24.

NHSPEG4

Figure 5:
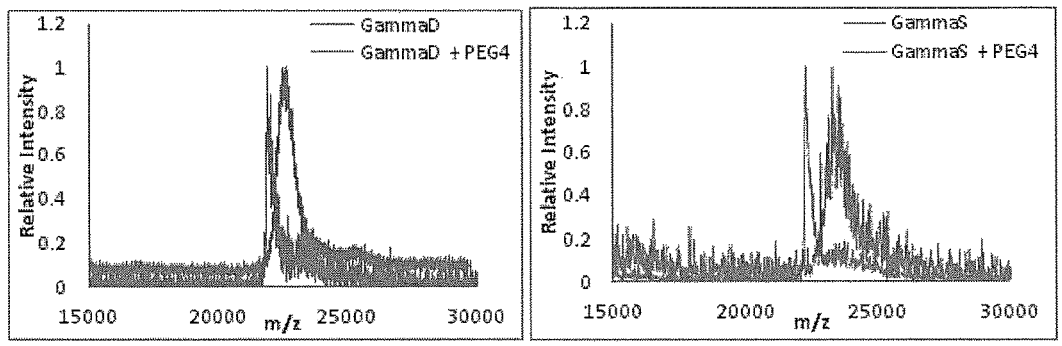

MALDI-TOF data showed an increase in the overall γ-crystallin molecular weight indicating modification with PEG4. (FIG. 5) The highest relative intensity seen for γ D-crystallin occurred at 22,820 m/z, while for γ S-crystallin this occurred at 23,329 m/z which correspond to 4 and 5 PEG4 units, respectively, being added to either protein. It should be noted that there is a Gaussian distribution around the relative intensity peak suggesting that there are proteins which contain both a greater and lesser degree of modification. MALDI-TOF data also showed that no unmodified crystallin protein is present.

CD spectroscopy again showed that PEGylation did not significantly affect the secondary structures of ɣ and α-crystallin proteins. (data not shown) Excellent agreement was seen between the native and PEG4 tailored ɣ-crystallin proteins.

Figure 6:
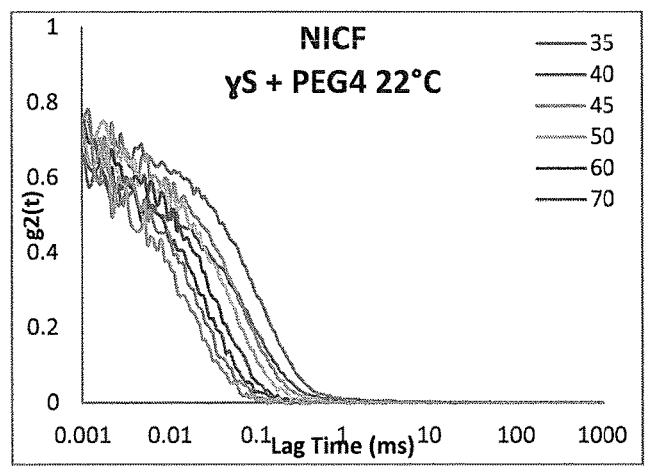
Figure 7:
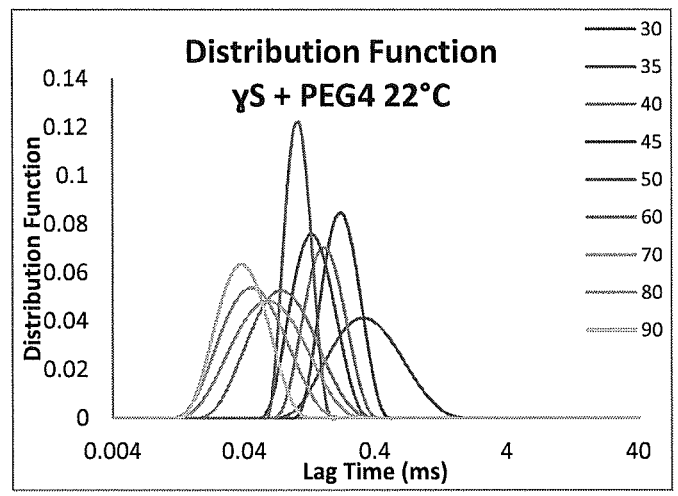
Figure 8:
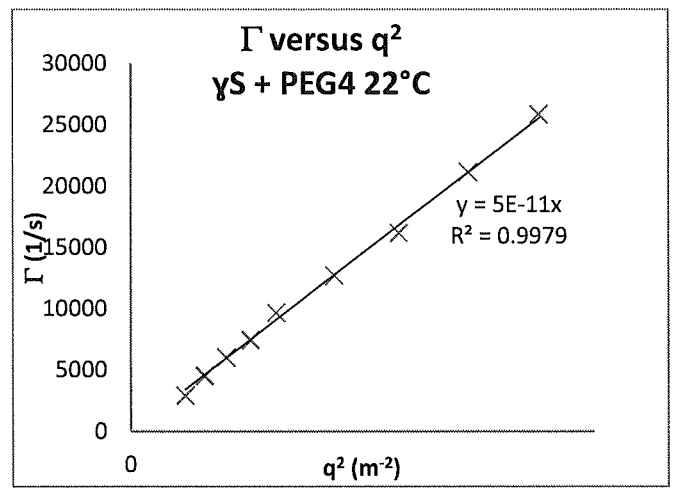

The NICF of ɣ-crystallin protein modified with PEG4 had a monoexponetial decay which indicates a single size scale present in solution. (FIG. 6) Similar to ɣ-crystallin modified with PEG24, no aggregate was present in solution. The distribution function (FIG. 7) again showed a single set of peaks that demonstrate linear angular dependence in the Γ versus $q^2$ graph (FIG. 8). The $R_h$ of ɣD-crystallin measured by DLS was 2.8 and 2.9 nm at 22° C. and 37° C. respectively. The $R_h$ size correlates well with the modified protein weight of nearly 22.8 kDa. A slight increase of the protein monomeric size can also been observed in DLS as the $R_h$ of the modified ɣD-crystallin protein is slightly larger than its unmodified predecessor. The PEG4 modified ɣS-crystallin protein had an $R_h$ of 2.9 at 22° C. and 37° C. The overall size of the modified protein did increase in comparison to unmodified ɣS-crystallin and the $R_h$ is consistent with a molecular weight of approximately 23.3 kDa.

ɣ-crystallin protein modified with NHSPEG4 and NHSPEG24 showed no aggregation at 22° and 37° C. Modification with PEG4 generally resulted in four to five low molecular weight additions while in the case of PEG24 two to three groups were added per ɣ-crystallin protein. The higher number of modifications made per protein with PEG4 provided no significant benefit in preventing aggregation. Similarly, adding a greater total weight with PEG24 to ɣ-crystallin provided no advantage to preventing aggregation.

The ɣ-crystallin proteins modified with PEG24 had a slightly larger $R_h$ in comparison to the PEG4 modification. As both modifications resulted in no aggregate it was concluded that spacer arm length does not significantly contribute to the prevention of aggregation. It is predicted that larger PEG chains would produce similar results.

Example 5—Chemical Modification of ɣD- and ɣS-Crystalline with CAPEG

Modification by CAPEG4 was performed to investigate an alternative reaction mechanism for the PEGylation of ɣ-crystallin. At physiological pH (6.8), the primary amine of CAPEG4 is slightly more positive and capable of reacting with the negatively charged amino acids, aspartic acid and glutamic acid. Alternatively, positively charged amino acids are still capable of reacting with the carboxylic acid of CAPEG4 (CA). CAPEG4 was selected for similar reasons as NHSPEG4, those being a small added molecular weight added per unit (265.3 g/mol) and a short spacer arm (1.81 nm).

CAPEG4

Figure 9:
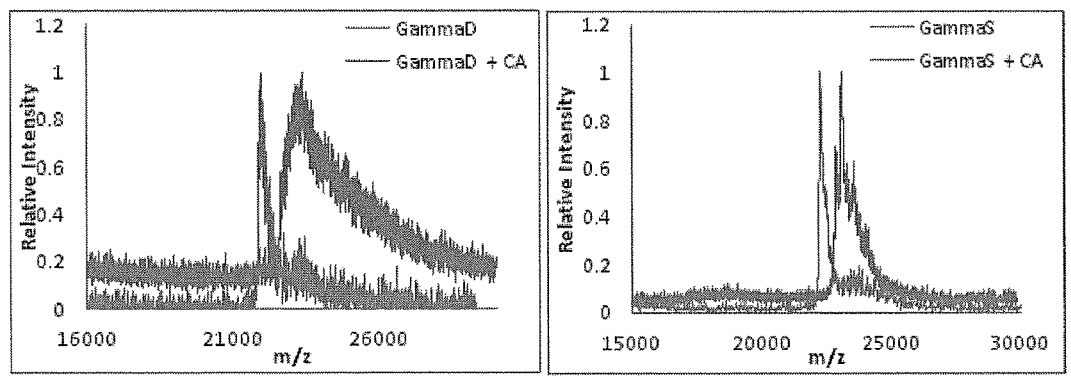

The MALDI-TOF showed a considerable increase in ɣ-crystallin molecular weight which is the result of modification by CAPEG4. (FIG. 9) There was no unmodified ɣ-crystallin in either solution which suggests that reaction conditions were sufficient for protein modification. The relative intensity peak at 23,273 m/z for ɣD-crystallin represents 5 CAPEG units having been added to the protein. A higher resolution MALDI-TOF spectrum for ɣS-crystallin showed several distinct mass peaks to include 22,867 m/z or 2 CAPEG4 units, a relative intensity maximum at 23,089 m/z or 3 CAPEG4 units, and 23,591 m/z or 5 CAPEG4 units.

The CD spectroscopy of CAPEG4 modification of ɣ-crystallin showed a similar trend to modifications made with PEG4 and PEG24. (Data not shown) ɣS-crystallin+CAPEG4 showed excellent correlation with the unmodified ɣS-crystallin protein. The modified ɣD-crystallin again showed a slight variation at 220 nm but overall the curve is of a similar shape as the native ɣD-crystallin.

Figure 10:
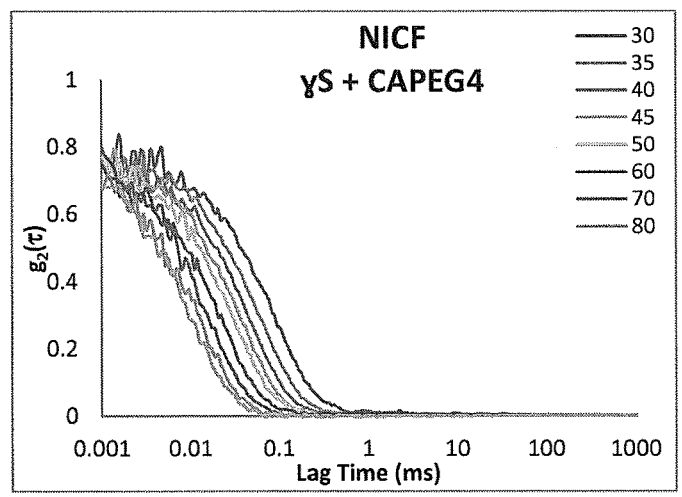
Figure 11:
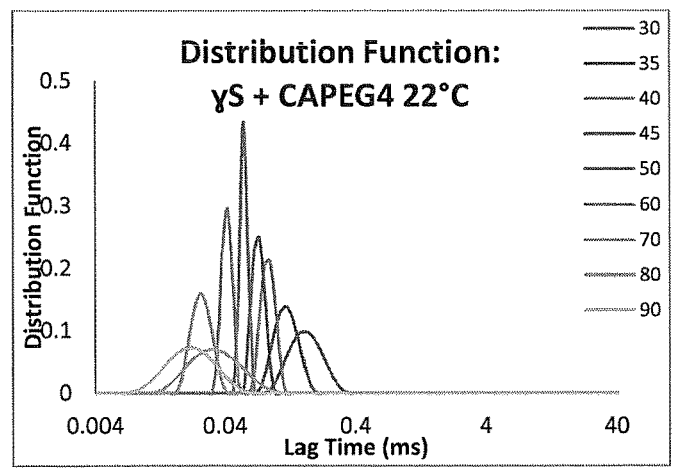
Figure 12:
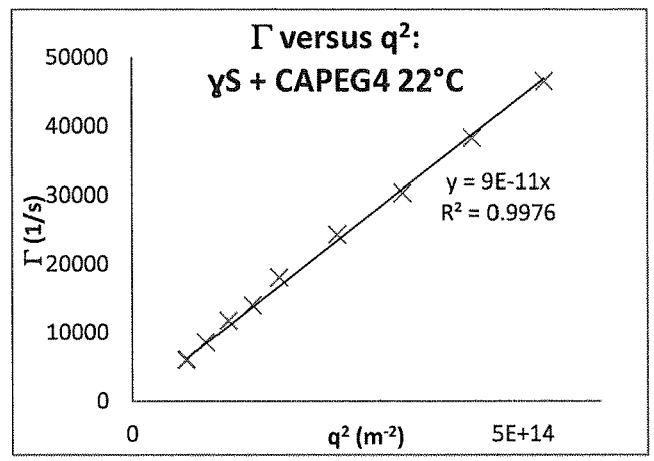

Modifying ɣ-crystallin with CAPEG also prevented aggregation of proteins. The NICF can be described by a monoexponetial function which produces a distribution function that has a linear Γ vs $q^2$ dependence. (FIG. 10-12) The modified ɣ-crystallin protein was seen in its monomeric form at both 22° and 37° C. where the $R_h$ was temperature independent. For ɣD-crystallin, the diffusion coefficient provided a calculated $R_h$ of 2.8 nm, while for ɣS-crystallin this value was 2.9 m. The $R_h$ values correlate well with the 23 kDa and 23.5 kDa modified molecular weights of ɣD- and ɣS-crystallin, respectively, in addition to being similar in size to ɣ-crystallin modified with PEG4.

PEGylation with CAPEG at physiological pH (6.8) targeted acidic amino acids. Similar to the reactions done with NHSPEG, the CAPEG modification should alter the overall surface charge of the protein. By reacting with negatively charged amino acids the hydrophilic PEG chain occupies the potentially charged amino acid. Having a similar size and number of modifications (four to five) as NHSPEG4, ɣ-crystallin tailored with CAPEG4 offers a very similar modification. A potential advantage to using CAPEG4 over NHSPEG is that there is no NHS leaving group in the reaction.

Without being held to theory, the CAPEG modification again suggests that the protein's surface charge is a key factor to the formation of ɣ-crystallin aggregates. As a PEG moiety is being added to the protein it is also possible that the hydrophobic nature of the surface is altered, preventing aggregation. The crucial information gained from this experiment is that modification through acidic or basic amino acids can prevent aggregation.

Example 6—Chemical Modification of ɣD- and ɣS-Crystalline with MMPEG

Maleimide functionalized PEG is yet another reaction mechanism by which the ɣ-crystallin proteins may be PEGylated. Thiol groups are capable of Michael addition over the double bond of the maleimide functional group. Both ɣ-crystallin proteins contain multiple cysteine amino acid residues which contain a thiol end group. PEGylation of ɣ-crystallin with MMPEG24 (MM) thus occurs by cysteine amino acids. Modification via this reaction mechanism is unique to previous PEGylation experiments because the overall protein charge should not be affected. In particular, MMPEG24 was chosen because the high molecular weight added per unit (1239.44 g/mol) and long spacer arm (9.53 nm) will be comparable with PEG24.

MMPEG24

The MALDI-TOF spectra of γ-crystallin modified with MMPEG24 showed three distinct peaks can be observed with minimal to no unmodified γ-crystallin. (data not shown) Four γD-crystallin peaks were observed at 23187, 24426, 25666 m/z corresponding to 1, 2, and 3 modifications. In the case of γS-crystallin peaks were observed at 23565, 24426, and 25666 m/z corresponding to 1, 2, and 3 modifications. The highest relative intensity for both crystallin proteins occurred at 2 modifications.

Excellent agreement is again seen between the native and PEGylated γ-crystallin proteins. It is known that in some instances the thiol groups of cysteine are involved in intramolecular disulfide bonding which give structural integrity providing the secondary structure. As both MM modified γD- and γS-crystallin spectra show a secondary structure similar to native γ-crystallin state it was concluded that the modification did not alter the proteins structure. (data not shown)

Figure 13:
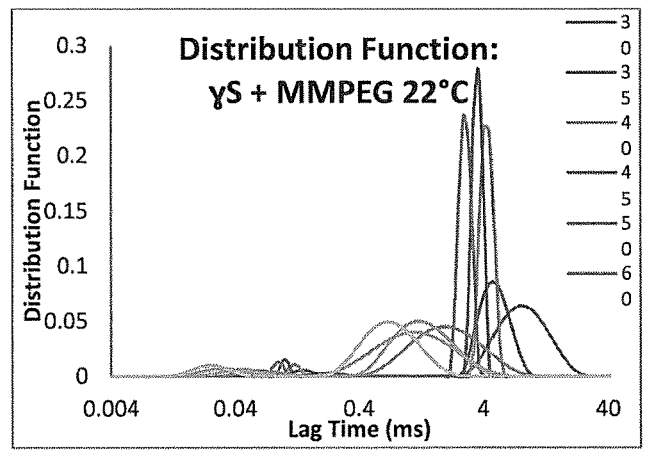

PEGylating γ-crystallin through its cysteine residues did not prevent aggregation. The NICF curves (data not shown) have an angular dependence which resulted in the distribution function having two distinct sets of peaks (FIG. 13). The $\Gamma$ versus $q^2$ graph showed two slopes with a linear angular dependence indicating the presence of a slow and fast diffusion coefficient. (data not shown) At 37° C., the slow mode resulted in an $R_h$ of 80 nm for γD-crystallin and 85 nm for γS-crystallin. The large size indicated that the protein was aggregating in solution. The fast mode corresponded to monomeric γ-crystallin protein, with an $R_h$ of 2.8 nm and 3.0 nm for γD- and γS-crystallin at 37° C.

The fact that PEGylation via maleimide functionality did not prevent aggregation provides critical information regarding the formation of γ-crystallin aggregates. Due to MMPPEG24 and NHSPEG24 both resulting in a similar number of modifications the surface coverage and spacer groups around the γ-crystallin proteins must also be similar. The aggregate observed with MMPEG24 modification demonstrates that prevention of aggregation cannot be not entirely dependent on hydrophilic spacer molecules.

A key insight into the aggregation mechanism is gained in realizing that PEGylating the protein via uncharged amino acids does not prevent aggregation. The key difference between MMPEG and NHSPEG or CAPEG is that PEGylation via maleimide reaction does not target charged amino acids of the protein. Without being held to theory, this suggests that surface charge and electrostatics play a major role in the formation of aggregates and must be targeted when disrupting aggregation.

Example 7—Chemical Modification of γD- and γS-Crystalline with BIOTIN

Biotin is a molecule commonly used for protein modification due to its high binding affinity for avidin. Proteins can be tagged with biotin, undergo reactions in vivo or in vitro, then be separated or purified from the bulk using an avidin column. The NHSBiotin molecule was chosen because it reacts through the same mechanism as PEG4 and PEG24 however the added molecule will no longer be hydrophilic but rather contain a highly charged end group. The molecular weight added per unit is 226.38 g/mole with a spacer arm of 1.38 nm.

NHSBiotin

The γ-crystallin proteins were successfully modified with biotin as shown in the MALDI-TOF. (data not shown) γD-crystallin's peak modification was eight units (23758 m/z) while γS-crystallin's peak occurrence was four units (23325 m/z). Both systems show no unmodified γ-crystallin indicating reaction conditions were sufficient for thorough modification.

The CD spectra showed a sizeable shift upwards as compared with the native structure of the protein. (data not shown) A shallower well was observed around 220 nm which goes against the trend of good correlation between modification and secondary structure. The change in spectra could be an indication that the secondary structure of the proteins has been perturbed by the modification. Despite the shift in spectra, the overall shape of the curve is similar and there was no indication of a disordered or random coil.

Figure 14:
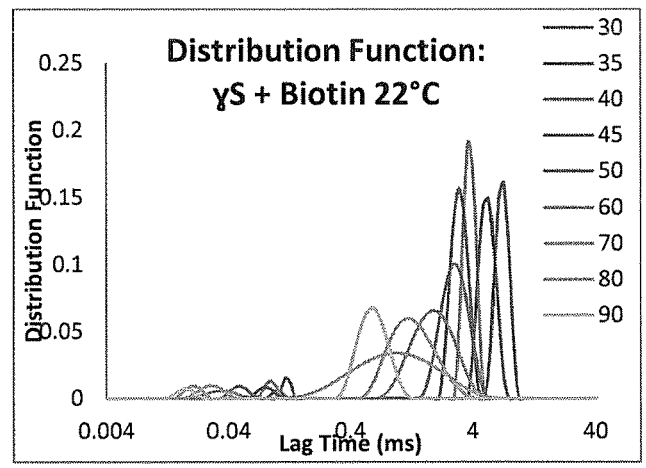

Aggregation of γ-crystallin protein was observed for γ-crystallin modified with biotin. The NICF showed a slow and a fast mode which resulted in the distribution function having two sets of peaks (FIG. 14). Angular dependence of the distribution function can be seen in the $\Gamma$ versus $q^2$ graph, where a qualitative difference was seen between the slow and fast modes. At 22° C., the $R_h$ of the fast and slow modes were 2.8 nm and 150 nm for γD-crystallin, while for γS-crystallin these values were 2.6 nm and 180 nm. A slow and fast mode was also observed at 37° C. with the $R_h$ values being similar to those at 22° C.

The aggregation of γ-crystallin modified with NHSBiotin shows that the functionality of the modifying molecule (i.e., the molecular bristle) is important. Mechanistically, biotin modified γ-crystallin in the same mannor as NHSPEG. Only modifying charged amino acids of γ-crystallin is thus not sufficient in preventing aggregation. A comparable degree of modification occurred with biotin and PEG4 meaning a similar shift of the protein's isoelectric point. Due to aggregation occurring in the case of γ-crystallin modified with biotin it is not sufficient to purely shift the isoelectric point of the γ-crystallin protein to prevent aggregation. DLS measurements of the biotinylated system also further support the notion that aggregation cannot be prevented merely by adding spacer molecules onto the surface of γ-crystallin.

The stark contrast in chemical properties between PEG and biotin is the reason one prevents aggregation and the other does not. PEG is a flexible hydrophilic molecule whereas the biotin functionally is capable of hydrogen bonding and stabilizing a negative charge. The properties of PEG thus help the solubility of proteins whereas biotin would contribute to the hydrophobic and electrostatic nature of the aggregates.

Example 8—Chemical Modification of γ D- and γ S-Crystalline with BIOTIN-PEG

Modifying γ-crystallin proteins with biotin resulted in aggregation so it was proposed to use NHSBiotinPEG which incorporates a hydrophilic spacer between the protein and biotin functionality. It was proposed that the hydrophilic nature of PEG would be the key factor in the prevention of γ-crystallin aggregation. The NHS functionalization is used to keep the reaction mechanism constant. The molecular weight added per unit was 825.64 g/mol and the spacer arm was 5.6 nm.

NHSBiotinPEG12

An appreciable shift in molecular weight was observed in MALDI-TOF indicating modification of the γ-crystallin proteins with BiotinPEG12. (data not shown) γ D-crystallin had three distinct peaks observable at 22760, 23582, and 24404 m/z corresponding to one, two, and three modifications. The resolution of γ S-crystallin provided MALDI-TOF peaks at 23001, 23816, 24669, 25470, and 26122 m/z corresponding to one-five modifications. The MALDI-TOF spectra also showed no unmodified γ-crystallin demonstrating sufficient reaction conditions.

The modified γ-crystallin protein's secondary structure was in good agreement with that of the native γ-crystallin as seen in the CD spectra. (data not shown) The well observed with CD spectra for γ-crystallin modified with just biotin was no longer evident. The PEG portion of the modification most likely allowed for increased solubility in addition to providing a spacer between the protein and biotin functionality.

Figure 15:
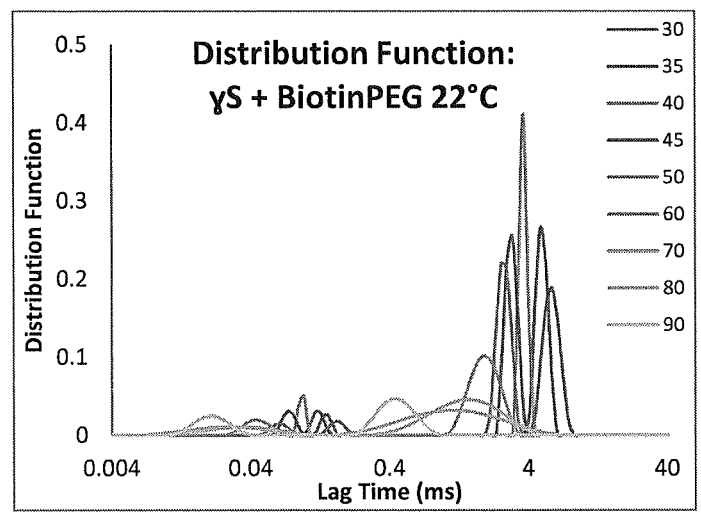

Despite the incorporation of PEG on the biotin functionality there was still aggregate present in solution as can be seen in the slow and fast mode of the NICF. (data not shown) The distribution function (FIG. 15) contained two sets of peaks that demonstrate an angular dependence. The Γ versus $q^2$ graph clearly showed two distinct linear fits, the slope of which provide a slow and fast diffusive mode. (data not shown) The fast diffusion coefficient corresponds to the monomeric γ-crystallin where γ D-crystallin had an $R_h$ of 2.7 nm at 22° C., while γ S-crystallin had the value was 2.6 nm. The slow diffusion coefficient represented the large aggregate present in solution with an $R_h$ of 105 nm for γ D-crystallin and 115 nm for γ S-crystallin at 22° C. Aggregate of a similar $R_h$ was also observed at 37° C.

The use of PEG as a spacer between the protein and biotin functionality did not aid in preventing aggregation. Without being held to theory and with reference to the discussion earlier concerning biotin shifting the isoelectric point of γ-crystallin, these experimental results also suggest hydrophobics to dominate over electrostatics in aggregates forming. The long spacer arm of BiotinPEG also did not prevent aggregation giving additional support to the trend of spacer molecule length not being a crucial factor in deterring aggregation. It should be noted that the γ-crystallin tailored with BiotinPEG has a slow mode or aggregate $R_h$ which was smaller than the biotin modification suggesting that PEG does aid in curbing aggregation.

Example 9—Chemical Modification of γ D- and γ S-Crystalline with Sulfo-N-hydroxysuccinimide Acetate (SA)

Due to previous modifications with large molecular weights and spacer arms still leading to aggregation, a minimally invasive modification was studied. The final modification was done with sulfo-N-hydroxysuccinimide acetate, which incorporated a minimal molecular weight (43 g/mol) and spacer arm (acetate molecule) per unit added. The reaction mechanism is similar to that of PEG4 so by reacting through the charged amino acid groups the isoelectric point of γ-crystallin should be affected.

A subtle shift in the weight of the γ-crystallin proteins was observed in MALDI-TOF. (data not shown) The peak relative intensity for γ D-crystallin occurred at 22209 m/z and for γ S-crystallin at 22562 m/z corresponding to six and seven acetate groups, respectively. The peaks showed no unmodified protein, indicating sufficient reaction conditions. A Gaussian distribution around the peak relative intensity indicated that some crystallin proteins have a higher and a lower degree of modification.

A CD spectrum for both modified γ-crystallin proteins demonstrated smaller well around 220 nm as compared to the native γ-crystallin. (data not shown) The change in CD spectra was also observed with the biotin modification. There is reason to believe that the secondary structure might be slightly affected by the modification although there are no indications of a random or disordered state.

Figure 16:
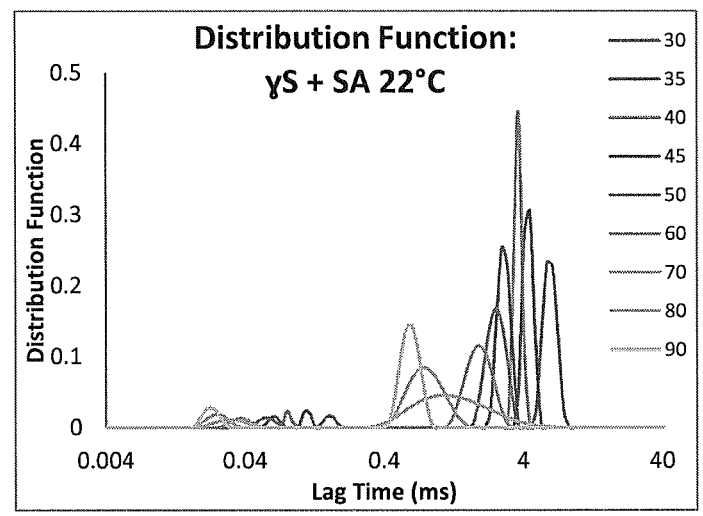

Looking at the NICF it is evident that modification of γ-crystallin with acetate groups did not prevent aggregation. (data not shown) The distribution function is shown in FIG. 16. The angular dependence of the slow and fast diffusive modes can be seen in the Γ versus $q^2$ graph. (data not shown) For γ D-crystallin at 37° C., the fast and slow diffusion coefficients correspond to an $R_h$ of 2.6 nm and 85 nm. The $R_h$ values for γ S-crystallin at 37° C. were 2.5 nm and 90 nm. The fast mode $R_h$ is an appropriate size for the modified γ-crystallin proteins whose molecular weight is approximately 22 kDa. $R_h$ values obtained from measurements made at room temperature showed similar results.

The SA modification was performed in an attempt to shift the protein's isoelectric point with a minimal spacer arm. Despite an aggregate being present in solution, the aggregate size was smaller in comparison to unmodified γ-crystallin.

Through a high number of modifications per protein it is possible that a substantial shift in isoelectric point did reduce the size of the aggregate. Without being held to theory, as aggregation is still present in solution it was concluded that the γ-crystallin protein's proximity to the isoelectric point is not solely responsible for the aggregation phenomena.

The results of Examples 3-9 are summarized in the following table:

TABLE 4

Summary of results with bifunctional charge masking agents

| | γS | | γD | |
|---|---|---|---|---|
| | $R_h$ (nm) | $R_h$ (nm) | $R_h$ (nm) | $R_h$ (nm) |
| PEG4 22° C. | 2.9 | | 2.8 | |
| PEG4 37° C. | 2.9 | | 2.9 | |
| PEG24 22° C. | 3.2 | | 3.1 | |
| PEG24 37° C. | 3.2 | | 3.1 | |
| CAPEG4 22° C. | 2.8 | | 2.9 | |
| CAPEG4 37° C. | 3 | | 2.8 | |
| MMPEG24 22° C. | 3.1 | 100 | 2.9 | 85 |
| MMPEG24 37° C. | 3 | 85 | 2.8 | 80 |
| Biotin 22° C. | 2.6 | 180 | 2.8 | 150 |
| Biotin 37° C. | 2.8 | 210 | 2.7 | 170 |
| BiotinPEG 22° C. | 2.6 | 115 | 2.7 | 105 |
| BiotinPEG 37° C. | 2.8 | 110 | 2.6 | 100 |
| SA 22° C. | 2.5 | 92.5 | 2.5 | 82.5 |
| SA 37° C. | 2.5 | 90 | 2.6 | 85 |

The results shown herein show that electrostatics are an important component of γ-crystallin aggregation. The electrostatic aggregation can be effectively interrupted using high salt concentrations or bifunctional charge masking agents. A increased understanding of the mechanism of γ-crystallin aggregation has provided a new class of agents that are particularly useful in the treatment of cataracts and presbyopia.

Methods: Harvesting and Characterization of Human Cadaver Lenses

Within about 24 hours of death, the eyeball is harvested, sliced and the vitreous is removed. The lens is excised and placed in an incubation medium called Optisol®. Optisol® is a corneal storage medium containing chondroitin sulfate, dextran 40, optisol base powder, sodium bicarbonate, gentamycin, amino acids, sodium pyruvate, L-glutamine, 2-mercaptoethanol and purified water. OD is the right eye and OS is the left eye.

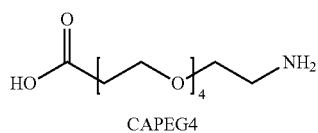

CAPEG4

Lens opacities are classified according to the LOCS III system. LOCS III measurements are taken with a slit lamp microscope. The LOCS III contains an expanded set of standards selected from the Longitudinal Study of Cataract slide library at the Center for Clinical Cataract Research, Boston, Mass. It includes six slit lamp images for grading nuclear color (NC) and nuclear opalescence (NO), five retroillumination images for grading cortical cataract (C), and five retroillumination images for grading posterior subcapsular (P) cataract. Cataract severity is graded on a decimal scale, with the standards have regularly spaced intervals on the scale.

Example 10: Testing of CAPEG4 in Human Cadaver Lenses-Transport Across the Epithelium The transport of the CAPEG4 across an epithelium construct was studied. The epithelium is the outer layer of the cornea and transport across the epithelium has proven to be challenging. The goal was to demonstrate the CAPEG4 construct could be used in a eye drop formulation for transport through the front of the eye.

Figure 19:
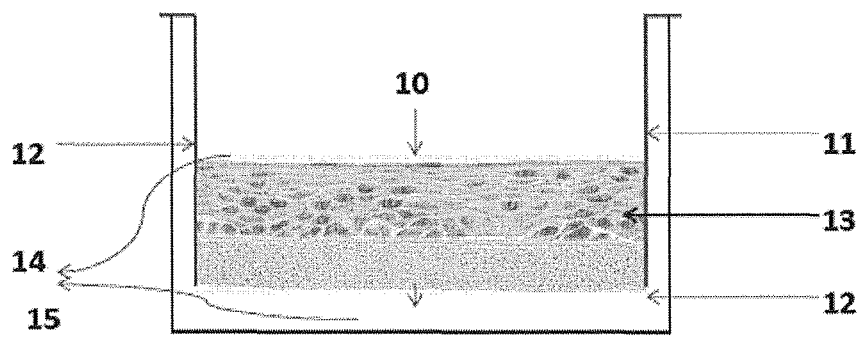
FIG. 19 shows a schematic of the measurement of trans-epithelial transport.
Figure 20:
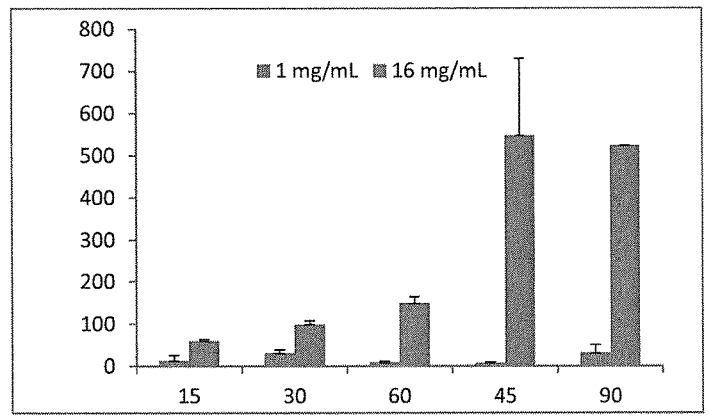
FIG. 20 shows the CAPEG4 that was transported to the bottom of the cell in the tran-epithelial transport experiment.

Specifically, the CAPEG4 construct in solution (10) was added to the top of an apparatus including a tissue culture plastic insert (11) containing culture medium (12) and an epithelium construct. (FIG. 19). The epithelium construct (13) consists of a layer(s) of human corneal epithelial cells (EpiOcular™ tissue (37° C., 5% $CO_2$). Aliquots were taken at the top (14) and the bottom (15) of the culture medium from 15 to 120 minutes for the analytical determination of $CA(PEG)_4$. FIG. 20 shows the CAPEG4 that was transported to the bottom of the cell.

Figure 21:
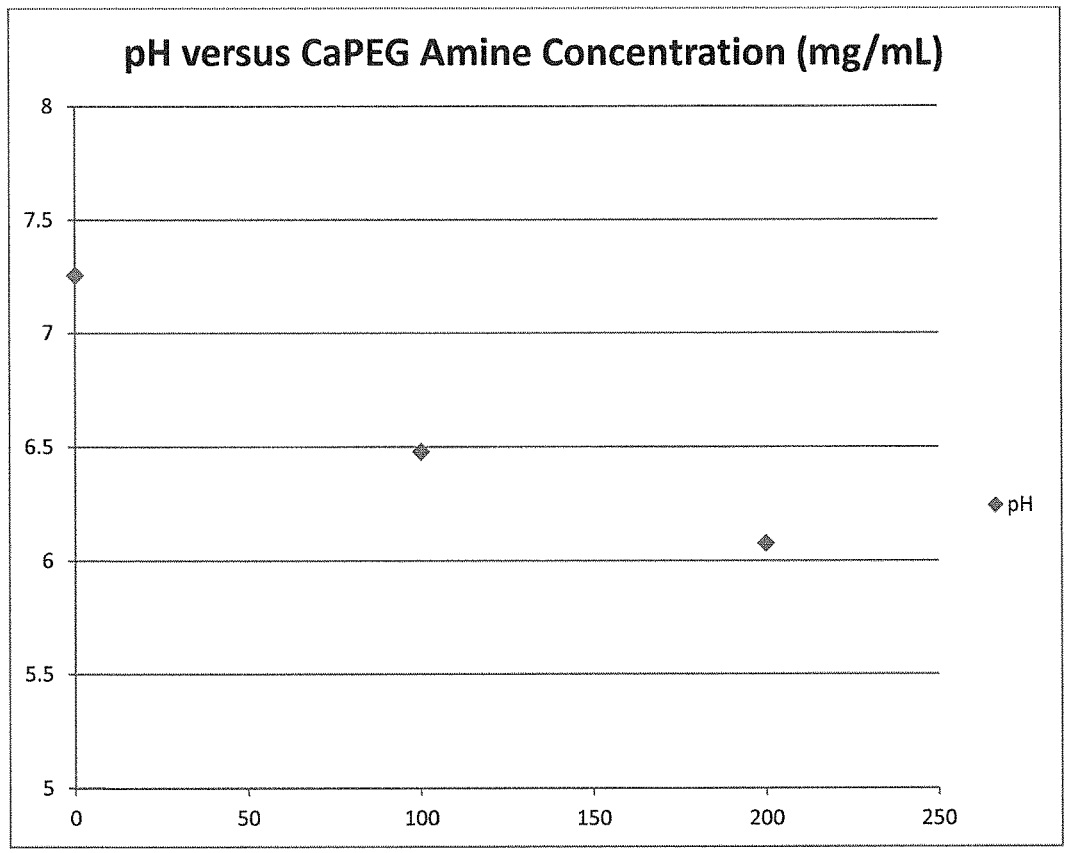
FIG. 21 shows the pH of Opisol® versus the mg/ml of added CAPEG4.

FIG. 21 shows the pH of Opisol® versus the mg/ml of added CAPEG4. The data is also presented in tables 5 and 6. Overall, it is demonstrated that the reduction in corticle and posterior subcapsular cataracts is due to the CAPEG4 and not a pH effect of the medium. because here was no reduction in corticle cataracts by simply changing (lowering) the pH of the Optisol® media with citric acid to the same pH of Optisol® containing the CaPEG amine. Reduction in opacity required the presence of the active agent.

TABLE 5

| 1 mg/ml CAPEG4 | | | | | |
|---|---|---|---|---|---|
| Time | Top | | Bottom | | |
| Min | mcg/well | Average | mcg/well | Average | % (stock) |
| 15 | 427 | 449 | 4 | 13 | 2.4 |
| | 472 | | 22 | | |
| 30 | 448 | 446 | 26 | 31 | 5.8 |
| | 445 | | 37 | | |
| 60 | 454 | 421 | 8 | 9 | 1.7 |
| | 388 | | 11 | | |
| 45 | 459 | 443 | 9 | 8 | 1.5 |
| | 428 | | 8 | | |
| 90 | 467 | 463 | 17 | 31 | 5.7 |
| | 459 | | 45 | | |
| 120 | 453 | 481 | 21 | 25 | 4.7 |
| | 510 | | 30 | | |
| 1000 mcg/mL | 543 | 543 | | | |
| Time 0 harvest: | 446 453 | 450 | 4 3 | 3 | 0.6 |

TABLE 6

| 16 mg/mL CAPEG4 | | | | | |
|---|---|---|---|---|---|
| Time | Top | | Bottom | | |
| Min | mcg/well | Average | mcg/well | Average | % (stock) |
| 15 | 5842 | 6375 | 58 | 60 | 0.7 |
| | 6908 | | 62 | | |
| 30 | 6099 | 6312 | 93 | 99 | 1.2 |
| | 6526 | | 105 | | |
| 60 | 6450 | 6972 | 160 | 149 | 1.8 |
| | 7494 | | 139 | | |

TABLE 6-continued

| 16 mg/mL CAPEG4 | | | | | |
|---|---|---|---|---|---|
| Time | Top | | Bottom | | |
| Min | mcg/well | Average | mcg/well | Average | % (stock) |
| 45 | 6313 | 6335 | 677 | 548 | 6.7 |
|  | 6356 |  | 418 |  |  |
| 90 | 6122 | 6457 | 525 | 525 | 6.4 |
|  | 6792 |  | na |  |  |
| 16000 mcg/mL | 8186 | 8186 |  |  |  |
| Blank insret at 15 min | 7857 | 7857 | 1837 | 1837 | 23 |

Example 11: Testing of CAPEG4 with Human Cadaver Lenses-Reduction of Cataracts in Human Cadaver Lenses In all cases, the control is Optisol® medium. The remaining data points are for isolated human cadaver lenses treated with CAPEG4 solutions with Optisol®.

Table 7 shows the results for lenses incubated with control medium or 10 mg/mL CAPEG4 versus time. In table 6, under the heading cortical, there is a LOCS III grade of 1.0, 1.0 and 0.9 for a lens incubated with 10 mg/ml CAPEG4. The LOCS grades for the control are 1.0, 1.2 and 0.9. At 10 mg/mL there was no significant change in the experimental versus control samples.

TABLE 7

LOCS III Grading of cataracts incubated with Optisol ® or 10 mg/ml CAPEG4 versus time

| [CaPEG] (mg/mL) | Time (HR) | Cortical | NO | NC | PS |
|---|---|---|---|---|---|
| 10 (OD) | 0 | 1.0 | 5.0 | 5.0 | 0.9 |
| Contol (OS) Optisol Only | 0 | 1.2 | 5.0 | 5.0 | 0.9 |
| 10 | 24 | 1.0 | 5.0 | 5.0 | 0.9 |
| Control Optisol Only | 24 | 1.2 | 5.0 | 5.0 | 0.9 |
| 10 | 72 | 0.9 | 5.0 | 5.0 | 0.9 |
| Control | 72 | 0.9 | 5.0 | 5.0 | 1.0 |

Table 8 shows the results for lenses incubated with control medium or 50 mg/mL CAPEG4 versus time. In table 7, under the heading cortical, there is a LOCS III grade of 1.0 for all samples and a Nuclear opalescence (NO) grade of 2.0 for all samples. There were no significant differences between the controls and 50 mg/mL incubation up to 72 hours for cortical cataracts or for NO. Nuclear color (NC) increased slightly with time for both the control and upon incubation in the 50 mg/mL CAPEG4 solution. There was a slight improvement in posterior subcapsular cataract from 1.1 to 0.9 at o and 24 hours, respectively.

TABLE 8

LOCS III Grading of cataracts incubated with Optisol ® or 50 mg/ml CAPEG4 versus time

| [CaPEG] (mg/mL) | Time (HR) | Cortical | NO | NC | PS |
|---|---|---|---|---|---|
| 50 (OD) | 0 | 1.0 | 2.0 | 1.7 | 1.1 |
| Contol (OS) Optisol Only | 0 | 1.0 | 2.0 | 1.8 | 0.9 |
| 50 | 24 | 1.0 | 2.0 | 1.7 | 0.9 |

TABLE 8-continued

LOCS III Grading of cataracts incubated with Optisol ® or 50 mg/ml CAPEG4 versus time

| [CaPEG] (mg/mL) | Time (HR) | Cortical | NO | NC | PS |
|---|---|---|---|---|---|
| Control Optisol Only | 24 | 1.0 | 2.0 | 1.8 | 0.9 |
| 50 | 72 | 1.0 | 2.0 | 1.9 | 0.9 |
| Control | 72 | 1.0 | 2.0 | 2.0 | 0.9 |

Table 9 shows the results for lenses incubated with control medium or 100 mg/mL CAPEG4 versus time. There is a decrease in opalescence (NO from 1.8 to 1.2) at 0 and 24 hours, respectively for CAPEG4 incubation and minor improvements in cortical and nuclear color up to 72 hours.

TABLE 9

LOCS III Grading of cataracts incubated with Optisol ® or 100 mg/ml CAPEG4 versus time

| [CaPEG] (mg/mL) | Time (HR) | Cortical | NO | NC | PS |
|---|---|---|---|---|---|
| 100 (OD) | 0 | 3.0 | 1.8 | 1.3 | 0.9 |
| Contol (OS) Optisol Only | 0 | 0.9 | 1.9 | 1.5 | 0.9 |
| 100 | 24 | 2.9 | 1.2 | 1.1 | 0.9 |
| Control Optisol Only | 24 | 0.9 | 1.8 | 2.0 | 0.9 |
| 100 | 72 | 2.7 | 1.2 | 1.1 | 0.9 |
| Control | 72 | 0.9 | 1.9 | 2.0 | 0.9 |

Table 10 is a repeat of the experiment in Table 8 with different eyes. Under PS (Posterior subcapsular cataracts) the sample incubated at 100 mg/ml CAPEG4 had values of 1.8, 1.5, and 1.0 at 0, 24 and 72 hours, respectively. There was also a reduction in cortical cataracts from 3.0 to 2.6 to 2.0 at 0, 24, and 72 hours, respectively.

TABLE 10

LOCS III Grading of cataracts incubated with Optisol ® or 100 mg/ml CAPEG4 versus time

| [CaPEG] (mg/mL) | Time (HR) | Cortical | NO | NC | PS |
|---|---|---|---|---|---|
| 100 (OD) | 0 | 3.0 | 3.0 | 3.0 | 1.8 |
| Contol (OS) Optisol Only | 0 | 1.0 | 3.0 | 3.0 | 1.5 |
| 100 | 24 | 2.6 | 3.0 | 3.0 | 1.5 |
| Control Optisol Only | 24 | 1.0 | 3.0 | 3.0 | 1.5 |
| 100 | 72 | 2.0 | 3.0 | 3.2 | 1.0 |
| Control | 72 | 1.0 | 3.0 | 3.1 | 1.5 |

Table 11 shows the results for lenses incubated with control medium or 200 mg/mL CAPEG4 versus time. Cortical cataracts were reduced from 2.5 to 2.2 to 2.0 at 0, 24, and 72 hours, respectively. The control also exhibit a slight reduction in cortical cataracts from 3.3 to 3.0 at 24 and 72 hours, respectively.

TABLE 11

LOCS III Grading of cataracts incubated with Optisol ® or 200 mg/ml CAPEG4 versus time

| [CaPEG] (mg/mL) | Time (HR) | Cortical | NO | NC | PS |
|---|---|---|---|---|---|
| 200 (OD) | 0 | 2.5 | 2.4 | 2.4 | 0 |
| Contol (OS) Optisol Only | 0 | 3.3 | 2.5 | 2.5 | 0 |
| 200 | 24 | 2.2 | 2.4 | 2.4 | 0 |
| Control Optisol Only | 24 | 3.3 | 2.5 | 2.5 | 0 |
| 200 | 72 | 2.0 | 2.4 | 2.4 | 0 |
| Control | 72 | 3.0 | 2.5 | 2.5 | 0 |

Table 12 shows the results for lenses incubated with control medium or 200 mg/mL CAPEG4 versus time. The only decrease in cataract was observed in cortical cataracts for the CAPEG4 solution going from 1.3 to 1.0 to 0.9 at 0, 24, and 72 hours, respectively.

TABLE 12

LOCS III Grading of cataracts incubated with Optisol ® or 200 mg/ml CAPEG4 (in Optisol ®) versus time

| [CaPEG] (mg/mL) | Time (HR) | Cortical | NO | NC | PS |
|---|---|---|---|---|---|
| 200 (OD) | 0 | 1.3 | 3.2 | 2.8 | 0.9 |
| Contol (OS) Optisol Only | 0 | 1.4 | 3.2 | 3.0 | 0.9 |
| 200 | 24 | 1.0 | 3.2 | 2.8 | 0.9 |
| Control Optisol Only | 24 | 1.4 | 3.2 | 3.0 | 0.9 |
| 200 | 72 | 0.9 | 3.2 | 2.8 | 0.9 |
| Control | 72 | 1.4 | 3.2 | 3.0 | 0.9 |

Table 13 shows the results of changing the pH of Optisol® with no added CAPEG4. The pH was lowered via the addition of citric acid. There was no effect of changing the pH of the Optisol® on the cataracts.

TABLE 13

Efect of pH of Optisol ® on cataracts

| pH | Time (HR) | Cortical | NO | NC | PS |
|---|---|---|---|---|---|
| 6.470 (OD) | 0 | 2.0 | 5.0 | 5.2 | 0.9 |
| 6.085 (OD) | 0 | 2.7 | 2.3 | 2.0 | 0.9 |
| 6.470 | 24 | 2.0 | 5.0 | 5.2 | 0.9 |
| 6.075 | 24 | 2.7 | 2.3 | 2.0 | 0.9 |
| 6.470 | 72 | 2.0 | 5.0 | 5.2 | 0.9 |
| 6.075 | 72 | 2.7 | 2.3 | 2.0 | 0.9 |

For cadaver lens studies, the different starting point for LOCSIII grade is due to the varying starting condition in the patients. As the concentration of the CAPEG4 solutions in Optisol increased, wrinkling of the lens capsule was observed and subjectively exhibited some loss of lens volume.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). All ranges disclosed herein are inclusive and combinable.

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

The invention claimed is:

1. An ophthalmic composition comprising
   at least one γ-crystallin charge masking agent, wherein the at least one γ-crystallin charge masking agent is a bifunctional molecule consisting of
      two different end groups selected from NH$_2$, methyl, a succinimide, a carboxylic acid, isocyanate, an isothiocyanate, a sulfonyl chloride, an aldehyde, a carbodiimide, an acyl azide, an anhydride, a fluorobenzene, a carbonate, an N-hydroxysuccinimide ester, an imidoester, an epoxide and a fluorophenyl ester,
      covalently linked to a molecular bristle that is a polyethylene glycol having 4 to 200 oxyethylene groups, an alkoxy-polyethylene glycol having 4 to 200 alkoxyethylene groups, an aryloxypolyethylene glycol having 4 to 200 aryloxyethylene groups, poly(2-hydroxypropyl)methacrylamide (HPMA), poly(2-hydroxyethyl)methacrylate (HEMA), a poly(2-oxaziline), poly(m-phosphocholine), poly lysine, or poly glutamic acid, the molecular bristle having a number average molecular weight of 150 to 8000, and
   an ophthalmically acceptable excipient.

2. The ophthalmic composition of claim 1, comprising NH$_2$, N-hydroxysuccinimide or COOH.

3. The ophthalmic composition of claim 1, comprising a polyethylene glycol, an alkoxy-polyethylene glycol, or an alkoxypolyethylene glycol having 4 to 200 oxyethylene, alkoxyethylene or aryloxyethylene groups.

4. The ophthalmic composition of claim 1, wherein the bifunctional molecule is

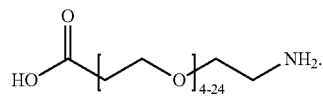

5. The ophthalmic composition of claim 1, wherein the bifunctional molecule is

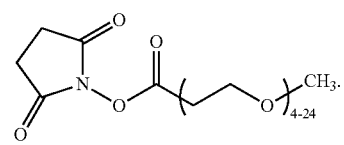

6. The ophthalmic composition of claim 1, wherein the ophthalmic composition is an eye drop, a suspension, a gel, an ointment, a spray, or an ophthalmic device.

7. The ophthalmic composition of claim 6, wherein the ophthalmic composition is in the form of an ophthalmic solution, an ophthalmic suspension, an ophthalmic ointment, or an ophthalmic gel.

8. The ophthalmic composition of claim 6, wherein the ophthalmic composition includes a buffering agent, an isotonizing agent, a solubilizer, a preservative, a viscosity-increasing agent, a chelating agent, an antioxidizing agent, an antibiotic, a sugar, a pH regulator, or a combination thereof.

9. The ophthalmic composition of claim 1, wherein the ophthalmic composition is an ophthalmic device.

10. The ophthalmic device of claim 9, in the form of a contact lens or a punctal plug.

11. The ophthalmic composition of claim 1, wherein the ophthalmic composition comprises the bifunctional molecule in an amount of about 0.001 g to about 0.1 g, or about 0.01 g to about 0.05 g.

12. The ophthalmic composition of claim 1, wherein the ophthalmic composition is a sustained release composition.

* * * * *